US008673986B2

(12) United States Patent
Cha et al.

(10) Patent No.: US 8,673,986 B2
(45) Date of Patent: Mar. 18, 2014

(54) COACERVATE HAVING AN IONIC POLYMER MIXED WITH THE ADHESIVE PROTEIN OF A MUSSEL OR OF A SPECIES OF THE VARIOME THEREOF

(75) Inventors: Hyung Joon Cha, Pohang (KR); Yoo Seong Choi, Seoul (KR); Dong Gyun Kang, Gangneung (KR); Young Hoon Song, Pohang (KR); Seonghye Lim, Daejeon (KR); Bong-Hyuk Choi, Daejeon (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/376,001

(22) PCT Filed: Aug. 6, 2010

(86) PCT No.: PCT/KR2010/005178
§ 371 (c)(1),
(2), (4) Date: Dec. 2, 2011

(87) PCT Pub. No.: WO2011/025158
PCT Pub. Date: Mar. 3, 2011

(65) Prior Publication Data
US 2012/0201748 A1 Aug. 9, 2012

(30) Foreign Application Priority Data

Aug. 25, 2009 (KR) .................. 10-2009-0078666
Aug. 5, 2010 (KR) .................. 10-2010-0075716
Aug. 5, 2010 (KR) .................. 10-2010-0075717

(51) Int. Cl.
*A61K 47/30* (2006.01)
(52) U.S. Cl.
USPC ..................................... 514/772.1
(58) Field of Classification Search
None
See application file for complete search history.

(56) References Cited

U.S. PATENT DOCUMENTS

| 7,947,806 | B2 * | 5/2011 | Cha et al. ............. 530/350 |
| 2009/0105449 | A1 | 4/2009 | Tomich et al. |
| 2009/0203883 | A1 | 8/2009 | Cha et al. |
| 2010/0120923 | A1 * | 5/2010 | Stewart et al. ......... 514/772.1 |

FOREIGN PATENT DOCUMENTS

| JP | 61-085400 | 4/1986 |
| JP | 09-225019 | 9/1997 |
| JP | 2009-084224 | 4/2009 |
| KR | 10-2004-0015532 | 2/2004 |
| WO | WO 2006/023207 A2 * | 3/2006 ........ A61K 47/48 |
| WO | 2006/107183 | 10/2006 |
| WO | 2008/150101 | 12/2008 |
| WO | 2009/029406 | 3/2009 |
| WO | 2009/094060 | 7/2009 |

OTHER PUBLICATIONS

Hwang, DS et al "Cell adhesion biomaterial based on mussel adhesive protein fused with RGD peptide." Biomaterials (Epub Jun. 14, 2007) 28(28): 4039-46.*
Hwang, Dong Soo et al. "Viscosity and interfacial properties in a mussel-inspired adhesive coacervate" (Jul. 21, 2010) 6(14): 3232-3236.*
Taylor, Steven W. "Chemoenzymatic Synthesis of Peptidyl 3,4-Dihydroxyphenylalanine for Structure-Activity Relationships in Marine Invertebrate Polypeptides" (2002) Analytical Biochemistry 302: 70-74.*
Mathiowitz E. Bioadhesive Drug Delivery Systems : Fundamentals, Novel Approaches, and Development [e-book]. Marcel Dekker; 1999. Available from: eBook Collection (EBSCOhost), Ipswich, MA. Accessed Dec. 18, 2012.*
Coleman, Ruth. "Types of Heparin" (Sep. 28, 2010) http://www.livestrong.com/article/252722-types-of-heparin/, accessed Dec. 21, 2012.*
Niels Holten-Andersen et al., Stiff Coatings on Compliant Biofibers: The Cuticle of Mytilus californianus Byssal Threads, Biochemistry, vol. 48, pp. 2752-2759, published online, Feb. 16, 2009.
Seonghye Lim et al., The adhesive properties of coacervated recombinant hybrid mussel adhesive proteins, Biomaterials, vol. 31, pp. 3715-3722, published online, Feb. 9, 2010.
Dong Soo Hwang, et al., "Promotion of osteoblast proliferation on complex coacervation-based hyaluronic acid—recombinant mussel adhesive protein coatings on titanium", Biomaterials, vol. 31, 2010, pp. 1080-1084 (Published online on Nov. 4, 2009).
Seonghye Lim, et al., "Complex Coacervation of Mussel Adhesive Protein with Hyaluronic Acid for microencapsulated bioadhesive system", K109, Trend of Biotechnology and Bioengineering XXV, The Korean Society for Biotechnology and Bioengineering, Nov. 2009, p. 127.
Cornelus G. de Kruif, et al., "Complex coacervation of proteins and anionic polysaccharides", Current Opinion in Colloid and Interface Science, London, GB, vol. 9, No. 5, pp. 340-349 (Dec. 1, 2004).

(Continued)

*Primary Examiner* — Karlheinz R Skowronek
*Assistant Examiner* — Mindy Newman
(74) *Attorney, Agent, or Firm* — Lexyoume IP Meister, PLLC.

(57) ABSTRACT

The present invention relates to a coacervate comprising a mussel adhesive protein and an anionic polymer, and more particularly, to a coacervate prepared by mixing a mussel adhesive protein with an anionic polymer, and a novel use thereof. In the present invention, a coacervate prepared by mixing a mussel adhesive protein and an anionic polymer shows a very excellent adhesive strength to various substrates such as cells or metals, and is able to maintain its adhesive strength in the presence of water or under water, thereby being effectively used as an adhesive. Moreover, it has an activity capable of encapsulating bioactive materials, thereby being effectively used as an active component of a composition for delivering bioactive materials.

27 Claims, 16 Drawing Sheets

(56) References Cited

OTHER PUBLICATIONS

Dong Soo Hwang, et al., "Cell adhesion biomaterial based on mussel adhesive protein fused with RGD peptide", Biomaterials, Elsevier Science Publishers BV., Barking, GB, vol. 28, No. 28, pp. 4039-4046 (Jul. 14, 2007).

Dong Soo Hwang, et al., "Practical recombinant hybrid mussel bioadhesive fp-151", Biomaterials, Elsevier Science Publishers, BV., Barking, GB, vol. 28, No. 24, pp. 3560-3568 (Aug. 1, 2007).

Dong Soo Hwang, et al., "Recombinant mussel adhesive protein Mgfp-5 as cell adhesion biometerial", Journal of Biotechnology, Elsevier Science Publishers, Amsterdam, NL, vol. 127, No. 4, pp. 727-735 (Dec. 22, 2006).

Dong Soo Hwang, et al., "Expression of functional recombinent mussel adhesive protein Mgfp-5 in *Escherichia coli*", Applied and Environmental Microbiology, American Society for Microbiology, US, vol. 70, No. 6, pp. 3352-3359 (Jun. 1, 2004).

European Patent Office, European search report of the corresponding European Patent Application No. 10812172.4 (Aug. 7, 2013).

* cited by examiner

SEQUENCE LISTING

<160> NUMBER OF SEQ ID NOS: 17

<210> SEQ ID NO 1
<211> LENGTH: 196
<212> TYPE: PRT
<213> ORGANISM: Artificial Sequence
<220> FEATURE:
<223> OTHER INFORMATION: FP-151 derived from Mytilus galloprovincialis

<400> SEQUENCE: 1

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
                20                  25                  30

Lys Pro Ser Tyr Pro Pro Thr Tyr Lys Ala Lys Pro Ser Tyr Pro Pro
            35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
                85                  90                  95

Tyr Tyr Gly Lys Ala Lys Lys Tyr Tyr Lys Tyr Lys Asn Ser Gly
                100                 105                 110

Lys Tyr Lys Tyr Leu Lys Lys Ala Arg Lys Tyr His Arg Lys Gly Tyr
                115                 120                 125

Lys Lys Tyr Tyr Gly Gly Ser Ser Ala Lys Pro Ser Tyr Pro Pro Thr
130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
                180                 185                 190

Pro Thr Tyr Lys
            195

<210> SEQ ID NO 2
<211> LENGTH: 202
<212> TYPE: PRT
<213> ORGANISM: Artificial Sequence
<220> FEATURE:
<223> OTHER INFORMATION: FP-151-RGD derived from Mytilus
      galloprovincialis

<400> SEQUENCE: 2

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
                20                  25                  30

Lys Pro Ser Tyr Pro Pro Thr Tyr Lys Ala Lys Pro Ser Tyr Pro Pro
            35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys

-continued

```
                        85                  90                  95
Tyr Tyr Gly Lys Ala Lys Lys Tyr Tyr Tyr Lys Tyr Lys Asn Ser Gly
            100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
                180                 185                 190

Pro Thr Tyr Lys Gly Arg Gly Asp Ser Pro
                195                 200

<210> SEQ ID NO 3
<211> LENGTH: 172
<212> TYPE: PRT
<213> ORGANISM: Artificial Sequence
<220> FEATURE:
<223> OTHER INFORMATION: FP-131 derived from Mytilus galloprovincialis

<400> SEQUENCE: 3

Met Ala Lys Pro Ser Tyr Pro Pro Thr Tyr Lys Ala Lys Pro Ser Tyr
  1               5                  10                  15

Pro Pro Thr Tyr Lys Ala Lys Pro Ser Tyr Pro Pro Thr Tyr Lys Ala
             20                  25                  30

Lys Pro Ser Tyr Pro Pro Thr Tyr Lys Ala Lys Pro Ser Tyr Pro Pro
         35                  40                  45

Thr Tyr Lys Ala Lys Pro Ser Tyr Pro Pro Thr Tyr Lys Pro Trp Ala
     50                  55                  60

Asp Tyr Tyr Gly Pro Lys Tyr Gly Pro Pro Arg Arg Tyr Gly Gly Gly
 65                  70                  75                  80

Asn Tyr Asn Arg Tyr Gly Arg Arg Tyr Gly Gly Tyr Lys Gly Trp Asn
                 85                  90                  95

Asn Gly Trp Lys Arg Gly Arg Trp Gly Arg Lys Tyr Tyr Gly Ser Ala
            100                 105                 110

Lys Pro Ser Tyr Pro Pro Thr Tyr Lys Ala Lys Pro Ser Tyr Pro Pro
            115                 120                 125

Thr Tyr Lys Ala Lys Pro Ser Tyr Pro Pro Thr Tyr Lys Ala Lys Pro
            130                 135                 140

Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
                165                 170

<210> SEQ ID NO 4
<211> LENGTH: 46
<212> TYPE: PRT
<213> ORGANISM: Artificial Sequence
<220> FEATURE:
<223> OTHER INFORMATION: FP-3 derived from Mytilus galloprovincialis

<400> SEQUENCE: 4

Ala Asp Tyr Tyr Gly Pro Lys Tyr Gly Pro Pro Arg Arg Tyr Gly Gly
  1               5                  10                  15

Gly Asn Tyr Asn Arg Tyr Gly Arg Arg Tyr Gly Gly Tyr Lys Gly Trp
```

```
                    20                  25                  30

Asn Asn Gly Trp Lys Arg Gly Arg Trp Gly Arg Lys Tyr Tyr
            35                  40                  45

<210> SEQ ID NO 5
<211> LENGTH: 76
<212> TYPE: PRT
<213> ORGANISM: Artificial Sequence
<220> FEATURE:
<223> OTHER INFORMATION: FP-5 derived from Mytilus galloprovincialis

<400> SEQUENCE: 5

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75

<210> SEQ ID NO 6
<211> LENGTH: 10
<212> TYPE: PRT
<213> ORGANISM: Artificial Sequence
<220> FEATURE:
<223> OTHER INFORMATION: fragment sequence derived from FP-1

<400> SEQUENCE: 6

Ala Lys Pro Ser Tyr Pro Pro Thr Tyr Lys
1               5                   10

<210> SEQ ID NO 7
<211> LENGTH: 60
<212> TYPE: PRT
<213> ORGANISM: Artificial Sequence
<220> FEATURE:
<223> OTHER INFORMATION: FP-1 derived from Mytilus galloprovincialis

<400> SEQUENCE: 7

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 8
<211> LENGTH: 3
<212> TYPE: PRT
<213> ORGANISM: Artificial Sequence
<220> FEATURE:
<223> OTHER INFORMATION: RGD Group 1 derived from extracellular matrix
      proteins

<400> SEQUENCE: 8

Arg Gly Asp
1
```

```
<210> SEQ ID NO 9
<211> LENGTH: 4
<212> TYPE: PRT
<213> ORGANISM: Artificial Sequence
<220> FEATURE:
<223> OTHER INFORMATION: RGD Group 2 derived from extracellular matrix
      proteins

<400> SEQUENCE: 9

Arg Gly Asp Ser
 1

<210> SEQ ID NO 10
<211> LENGTH: 4
<212> TYPE: PRT
<213> ORGANISM: Artificial Sequence
<220> FEATURE:
<223> OTHER INFORMATION: RGD Group 3 derived from extracellular matrix
      proteins

<400> SEQUENCE: 10

Arg Gly Asp Cys
 1

<210> SEQ ID NO 11
<211> LENGTH: 4
<212> TYPE: PRT
<213> ORGANISM: Artificial Sequence
<220> FEATURE:
<223> OTHER INFORMATION: RGD Group 4 derived from extracellular matrix
      proteins

<400> SEQUENCE: 11

Arg Gly Asp Val
 1

<210> SEQ ID NO 12
<211> LENGTH: 10
<212> TYPE: PRT
<213> ORGANISM: Artificial Sequence
<220> FEATURE:
<223> OTHER INFORMATION: RGD Group 5 derived from extracellular matrix
      proteins

<400> SEQUENCE: 12

Arg Gly Asp Ser Pro Ala Ser Ser Lys Pro
 1               5                  10

<210> SEQ ID NO 13
<211> LENGTH: 5
<212> TYPE: PRT
<213> ORGANISM: Artificial Sequence
<220> FEATURE:
<223> OTHER INFORMATION: RGD Group 6 derived from extracellular matrix
      proteins

<400> SEQUENCE: 13

Gly Arg Gly Asp Ser
 1               5

<210> SEQ ID NO 14
<211> LENGTH: 6
<212> TYPE: PRT
<213> ORGANISM: Artificial Sequence
<220> FEATURE:
<223> OTHER INFORMATION: RGD Group 7 derived from extracellular matrix
      proteins

<400> SEQUENCE: 14
```

```
Gly Arg Gly Asp Thr Pro
1               5

<210> SEQ ID NO 15
<211> LENGTH: 6
<212> TYPE: PRT
<213> ORGANISM: Artificial Sequence
<220> FEATURE:
<223> OTHER INFORMATION: RGD Group 8 derived from extracellular matrix
      proteins

<400> SEQUENCE: 15

Gly Arg Gly Asp Ser Pro
1               5

<210> SEQ ID NO 16
<211> LENGTH: 7
<212> TYPE: PRT
<213> ORGANISM: Artificial Sequence
<220> FEATURE:
<223> OTHER INFORMATION: RGD Group 9 derived from extracellular matrix
      proteins

<400> SEQUENCE: 16

Gly Arg Gly Asp Ser Pro Cys
1               5

<210> SEQ ID NO 17
<211> LENGTH: 5
<212> TYPE: PRT
<213> ORGANISM: Artificial Sequence
<220> FEATURE:
<223> OTHER INFORMATION: RGD Group 10 derived from extracellular matrix
      proteins

<400> SEQUENCE: 17

Tyr Arg Gly Asp Ser
1               5
```

COACERVATE HAVING AN IONIC POLYMER MIXED WITH THE ADHESIVE PROTEIN OF A MUSSEL OR OF A SPECIES OF THE VARIOME THEREOF

TECHNICAL FIELD

The present invention relates to a coacervate comprising a mussel adhesive protein and an anionic polymer, and more particularly, to a coacervate prepared by mixing a mussel adhesive protein with an anionic polymer, and a novel use thereof.

BACKGROUND ART

Marine mussels produce and secrete adhesive proteins that allow them to tightly attach themselves to wet solid surfaces such as underwater rocks, and thus fight tidal currents or buoyancy in the aqueous saline environment (J. H. Waite et al., 1983, Biological Review 58, 209-231; H. J. Cha et al., 2008, Biotechnology Journal 3, 631-638).

Mussel adhesive proteins are known as the most powerful natural adhesives, compared to the currently known chemical synthetic adhesives. Even though mussel adhesive proteins have an approximately two times higher tensile strength than epoxy resins, they are flexible. In addition, mussel adhesive proteins can also attach to various substances, including plastic, glass, metals, Teflon, and biological substances, and anchor to wet surfaces within a few minutes. These properties still remain unsolved in the fields of chemical adhesives. Mussel adhesive proteins can also be of particular value in medical applications such as adhesion of tissues or broken teeth, because they do not attack the human cells or do not impose immunogenicity (J. Dove et al., 1986, Journal of American Dental Association 112, 879).

In particular, mussel adhesive proteins can be used in cell surface adhesion technology, which is one of very important technologies required in the fields of cell culture and tissue engineering. That is, the technology is to efficiently attach cells on the surface for the cell and tissue cultures, and thus the technology is very important in promoting cell proliferation and differentiation (M. Tirrell et al., 2002, Surf. Sci., 500, 61-83).

Since naturally extracted mussel adhesive materials show high cell-adhesion ability and greatly promote cell proliferation and differentiation, compared with other coating methods, they are commercially used. However, there is a problem in that 10,000 mussels are required for 1 g of naturally extracted materials (C. V. Benedict et al., 1989, Adhesives from renewable resources, No. 385, 452-483).

Accordingly, there is a need to develop an efficient method of utilizing the mussel adhesive proteins, compared to the known methods, in particular, a method applicable to cell surface adhesion technology by improvement of cell adhesion activity.

Meanwhile, coacervate is one of the colloidal materials formed by mixing an anionic polymer electrolyte and a cationic polymer electrolyte under particular conditions. When a coacervate is formed, absorbance of a solution increases, and it forms a spherical droplet to be separated from the solution. Upon coacervation, the participating electrolyte is separated from the solution, and condensed to exist as a liquid phase. At this time, its physical properties are changed, including reduced surface tension and increased viscosity. Coacervation also occurs by mixing a protein with an oppositely charged polyelectrolyte (C. G. de Kruif et al., 2004, Current Opinion in Colloid and Interface Science 9, 340-349). Owing to low surface tension, coacervation is also employed for the microencapsulation of functional materials such as drugs, enzymes, cells, food additives or the like (Schmitt C. et al., 1998, Critical Review in Food Science and Nutrition 8, 689-753).

However, there are no studies, regarding the formation of coacervates from mussel adhesive proteins and the use of mussel adhesive proteins for the delivery of bioactive materials.

DISCLOSURE

Technical Problem

Accordingly, the present inventors found that a coacervate prepared by mixing a cationic mussel adhesive protein and an anionic polymer has a more excellent adhesive activity than single mussel adhesive proteins, and it can be used for the delivery of bioactive materials, thereby completing the present invention.

Technical Solution

Therefore, an object of the present invention is to provide a coacervate including a mussel adhesive protein or a mutant thereof together with an anionic polymer.

Further, another object of the present invention is to provide an adhesive including the coacervate.

Further, still another object of the present invention is to provide a composition for delivering bioactive materials, including the coacervate.

Further, still another object of the present invention is to provide a delivery vehicle for bioactive materials, characterized in that (a) the coacervate and the bioactive material are included, and (b) the bioactive material is encapsulated inside the coacervate.

Further, still another object of the present invention is to provide a method for preparing a delivery vehicle for bioactive materials, including the steps of (a) mixing a mussel adhesive protein or a mutant thereof with an anionic polymer and a bioactive material, and (b) forming a layer surrounding the bioactive material by a coacervate that is prepared by the mussel adhesive protein or the mutant thereof and the anionic polymer.

Further, still another object of the present invention is to provide a method for preparing a coacervate, including the step of mixing a mussel adhesive protein or a mutant thereof with an anionic polymer at pH 2.0 to pH 10.0 and a weight ratio of 1:0.01 to 1:10.

Further, still another object of the present invention is to provide the use of the coacervate of the present invention in adhesion.

Further, still another object of the present invention is to provide a method for using the coacervate of the present invention in adhesion, including the steps of (a) preparing the coacervate of the present invention and (b) adhering the coacervate to a substrate.

Further, still another object of the present invention is to provide the use of the coacervate of the present invention for the delivery of bioactive materials.

Further, still another object of the present invention is to provide a method for using the coacervate of the present invention for the delivery of bioactive materials, including the steps of (a) preparing the coacervate of the present invention and (b) encapsulating a bioactive material inside the coacervate.

Further, still another object of the present invention is to provide the use of the coacervate of the present invention in the preparation of a delivery vehicle for bioactive materials.

Further, still another object of the present invention is to provide a method for using the coacervate of the present invention in the preparation of a delivery vehicle for bioactive materials, including the steps of (a) preparing the coacervate of the present invention and (b) encapsulating the bioactive material inside the coacervate.

Best Mode

In order to achieve the above objects, the present invention provides a coacervate including a mussel adhesive protein or a mutant thereof together with an anionic polymer.

Further, the present invention provides an adhesive including the coacervate.

Further, the present invention provides a composition for delivering bioactive materials, including the coacervate.

Further, the present invention provides a delivery vehicle for bioactive materials, characterized in that (a) the coacervate and the bioactive material are included, and (b) the bioactive material is encapsulated inside the coacervate.

Further, the present invention provides a method for preparing a delivery vehicle for bioactive materials, including the steps of (a) mixing a mussel adhesive protein or a mutant thereof with an anionic polymer and a bioactive material, and (b) forming a layer surrounding the bioactive material by a coacervate that is prepared by the mussel adhesive protein or the mutant thereof and the anionic polymer.

Further, the present invention provides a method for preparing a coacervate, including the step of mixing a mussel adhesive protein or a mutant thereof with an anionic polymer at pH 2.0 to pH 10.0 and a weight ratio of 1:0.01 to 1:10.

Further, the present invention provides the use of the coacervate of the present invention in adhesion.

Further, the present invention provides a method for using the coacervate of the present invention in adhesion, including the steps of (a) preparing the coacervate of the present invention and (b) adhering the coacervate to a substrate.

Further, the present invention provides the use of the coacervate of the present invention for the delivery of bioactive materials.

Further, the present invention provides a method for using the coacervate of the present invention for the delivery of bioactive materials, including the steps of (a) preparing the coacervate of the present invention and (b) encapsulating a bioactive material inside the coacervate.

Further, the present invention provides the use of the coacervate of the present invention in the preparation of a delivery vehicle for bioactive materials.

Further, the present invention provides a method for using the coacervate of the present invention in the preparation of a delivery vehicle for bioactive materials, including the steps of preparing the coacervate of the present invention and (b) encapsulating the bioactive material inside the coacervate.

Hereinafter, the present invention will be described in detail.

In the present invention, the mussel adhesive protein is an adhesive protein derived from mussels, and preferably includes all mussel adhesive proteins described in WO2006/107183A1 or WO 2005/092920, but is not limited thereto.

Preferably, the mussel adhesive protein may be (a) a polypeptide consisting of an amino acid sequence of SEQ ID NO. 4, (b) a polypeptide consisting of an amino acid sequence of SEQ ID NO. 5, (c) a polypeptide consisting of 1 to 10 consecutive amino acid sequences of SEQ ID NO. 6, and (d) a fusion polypeptide of two or more polypeptides selected from the group consisting of the polypeptides of (a), (b), and (c). In (c), the polypeptide is, but not limited to, preferably a polypeptide consisting of an amino acid sequence of SEQ ID NO. 7. In (d), the fusion polypeptide is, but not limited to, preferably a polypeptide consisting of an amino acid sequence of SEQ ID NO. 1 or SEQ ID NO. 3.

In the present invention, the mutants of the mussel adhesive protein may be preferably those including an additional sequence at the carboxyl-terminus or amino-terminus of the mussel adhesive protein or those including substitution of some amino acids of the mussel adhesive protein with other amino acids, as long as they retain an adhesive strength of the mussel adhesive protein. More preferably, the mutants of the mussel adhesive protein may be polypeptide linkages consisting of 3 to 25 amino acids including RGD at the carboxyl-terminus or amino-terminus of the mussel adhesive protein or polypeptides where 1 to 100%, preferably 5 to 100% of tyrosine residues of the mussel adhesive protein are substituted with 3,4-dihydroxyphenyl-L-alanine (DOPA).

The 3 to 25 amino acids including RGD are, but not limited to, preferably one or more selected from the group consisting of RGD (Arg Gly Asp, SEQ ID NO. 8), RGDS (Arg Gly Asp Ser, SEQ ID NO. 9), RGDC (Arg Gly Asp Cys, SEQ ID NO. 10), RGDV (Arg Gly Asp Val, SEQ ID NO. 11), RGDSPASSKP (Arg Gly Asp Ser Pro Ala Ser Ser Lys Pro, SEQ ID NO. 12), GRGDS (Gly Arg Gly Asp Ser, SEQ ID NO. 13), GRGDTP (Gly Arg Gly Asp Thr Pro, SEQ ID NO. 14), GRGDSP (Gly Arg Gly Asp Ser Pro, SEQ ID NO. 15), GRGDSPC (Gly Arg Gly Asp Ser Pro Cys, SEQ ID NO. 16) and YRGDS (Tyr Arg Gly Asp Ser, SEQ ID NO. 17).

The mutant of the mussel adhesive protein which is a polypeptide linkage consisting of 3 to 25 amino acids including RGD at the carboxyl-terminus or amino-terminus of the mussel adhesive protein is, but not limited to, preferably a polypeptide consisting of an amino acid sequence of SEQ ID NO. 2.

The mussel adhesive protein of the present invention is preferably inserted into commonly used expression vectors that are constructed for expressing exogenous genes, and mass-produced through genetic engineering methods, but is not limited thereto. The above vector may be suitably selected according to the type and characteristics of the host cell used in the protein production, or it may be newly constructed. Transformation of the vector into the host cell and production of the recombinant protein from the transformant can be easily carried out through ordinarily employed methods. A method of selecting, constructing, transforming the vector and a method of expressing the recombinant protein can be easily carried out by an ordinary person skilled in the art, and partial variations in the ordinarily employed methods are also included in the present invention.

In the present invention, any polymer material may be used as the anionic polymer without limitation, as long as it is able to bind with the cationic mussel adhesive protein to form a coacervate. Preferably, the anionic polymer may be a polymer having a pI (Isoelectric point) lower than that of the cationic mussel adhesive protein, more preferably, a polymer having a pI of 2 to 6, and much more preferably, a polymer having a pI of 2 to 4.

For example, the anionic polymer of the present invention may be one or more selected from the group consisting of hyaluronic acid, ferredoxin, poly styrene sulfonic acid, gum arabic, gelatin, albumin, carbopol, high or low methoxyl pectin, sodium carboxymethyl guar gum, xanthan gum, whey protein, faba bean legumin, carboxymethyl cellulose, alginate, carrageenan, sodium hexametaphosphate, sodium casinate, hemoglobin, heparin and exopolysaccharide B40. An average molecular weight of the anionic polymer may be, but not limited to, preferably selected from 1 kDa to 300 kDa, more preferably from 10 kDa to 100 kDa, much more preferably from 17 kDa to 59 kDa, and most preferably 17 kDa, 35 kDa or 59 kDa. If the molecular weight is not within the above range, coacervation may not occur.

In the present invention, the bioactive material is a material exerting a specific pharmacological action when administered into the body or applied to the skin surface. The bioactive material is, but not limited to, preferably one or more selected from the group consisting of drugs, enzymes, cells and food additives, and more preferably one or more selected from the group consisting of anticancer agents, antibiotics, anti-inflammatory agents, hormones, hormone antagonists, interleukins, interferons, growth factors, tumor necrosis factors, endotoxins, lymphotoxins, urokinase, streptokinase, tissue plasminogen activators, protease inhibitors, alkylphosphocoline, radioactive isotopes, surfactants, cardiovascular pharmaceutic products, gastrointestinal pharmaceutic products, and neuropharmaceutic products. The anti-inflammatory agents may be, but is not limited to, preferably dexamethasone.

In the present invention, the coacervate refers to a colloid produced by mixing the mussel adhesive protein or the mutant thereof with an anionic polymer.

The coacervate of the present invention is characterized by including the mussel adhesive protein or the mutant thereof together with the anionic polymer. The coacervate may be formed by mixing the cationic mussel adhesive protein or the mutant thereof with the anionic polymer.

The coacervate of the present invention may be preferably prepared in an aqueous solvent, more preferably in methanol, ethanol, propanol, acetone, or acetic acid aqueous solution, still more preferably in acetic acid aqueous solution, yet still more preferably in 0.1% to 10% acetic acid aqueous solution, and most preferably in 0.5 to 8% acetic acid aqueous solution, but is not limited thereto.

When the coacervate of the present invention is prepared in the above solvent, an optimal pH is, but not limited to, preferably pH 2.0 to pH 10.0, more preferably pH 2.0 to pH 6.0, and most preferably pH 2.5 to pH 5.5. If the pH is not within the above range, coacervation may not occur, or polymer deformation may occur.

Each of the mussel adhesive protein or the mutant thereof and the anionic polymer is preferably added to the above solvent at a ratio of 0.001 to 100% (w/v), and more preferably 0.01 to 30% (w/v) based on the total volume of the solvent, but is not limited thereto.

The coacervate of the present invention may be preferably prepared by mixing the mussel adhesive protein or the mutant thereof and the anionic polymer at a weight ratio of 1:0.01 to 1:10, more preferably at a weight ratio of 1:0.25 to 1:2.5, and most preferably at a weight ratio of 1:0.25 to 1:2.33, but is not limited thereto. If the weight ratio is not within the above range, coacervation may not occur effectively.

The coacervate prepared by mixing the mussel adhesive protein or the mutant thereof and the anionic polymer is very excellent in terms of cell adhesive activity, compared to the known mussel adhesive proteins or poly-L-lysine known to have a cell adhesive activity.

In one embodiment of the present invention, a cell culture plate is coated with the coacervate, and *drosophila* S2 cells are cultured in the coated cell culture plate. Then, the plate is washed with PBS (phosphate buffered saline), and MTT (3-(4,5-dimethylthiazol-2-yl)-2,5-diphenyltetrazolium bromide) assay is performed to determine the number of cells adhered to the plate for the assessment of cell adhesive activity. As a result, it was found that the coacervate prepared by mixing the mussel adhesive protein and the anionic polymer is very excellent in terms of cell adhesive activity, compared to the known mussel adhesive proteins or poly-L-lysine known to have a cell adhesive activity (see <Example 3>).

Further, the coacervate of the present invention maintains its effective adhesive strength in a bulk adhesive system, for example, adhesion of metals such as aluminum, as well as in a micro-adhesive system such as cell adhesive activity.

In one embodiment of the present invention, when the coacervate of the present invention is used, it maintains an adhesive strength approximately twice higher than a single mussel adhesive protein. In particular, when a crosslinking agent, tyrosinase or glutaraldehyde is added, it is able to maintain an excellent adhesive strength even in the presence of water or under water (see <Example 4>).

Therefore, the coacervate prepared by mixing the mussel adhesive protein or the mutant thereof and the anionic polymer can be used for adhesion.

The adhesive of the present invention is characterized by including the coacervate.

The adhesive may further include 0.0001 to 99% by weight of an excipient that is generally contained in bioadhesives or is pharmaceutically acceptable. Examples of the excipients include surfactants, oxidants, crosslinking agents, and fillers, but are not limited thereto (see: US Patent Application Publication No. 2003-65060 and U.S. Pat. No. 5,015,677). The surfactant may be cationic, anionic, non-ionic, or amphoteric, and exemplified by sodium dodecylsulfate and sodium dodecylbenzensulfonate. The oxidant may be selected from the group consisting of catechol oxidase, formaldehyde, bis(sulfosuccinimidyl) suberate, 3,3'-Dithiobis(sulfosuccinimidyl propionate), $O_2$, $Fe^{3+}$, $H_2O_2$ and $IO^{4-}$ (see Macromolecules 1998, 31, 4739-4745) and the filler may be selected from the group consisting of collagen, hyaluronic acid, condroitan sulfate, elastine, laminin, caseine, hydroxyapatite, albumin, fibronectin, and hybrin.

In particular, the crosslinking agent may be tyrosinase or glutaldehyde. With respect to the addition amount of the crosslinking agent, tyrosinase may be added at 0.0001 to 1% by weight, preferably 0.001 to 1% by weight, and more preferably 0.01 to 1% by weight, based on the weight of the mussel adhesive protein or the mutant thereof, and glutaraldehyde may be added at 0.001 to 5% by volume, more preferably 0.01 to 5% by volume, and most preferably 0.1 to 5% by volume, based on the total volume of the adhesive solution.

When the adhesive of the present invention is applied in the presence of water or under water, the preferred crosslinking agent is, but not limited to, glutaraldehyde.

The adhesive of the present invention maintains its effective adhesive strength in a bulk adhesive system, for example, adhesion of metals such as aluminum, as well as in a micro-adhesive system such as cell adhesive activity (see <Example 3> and <Example 4>).

Further, since the adhesive of the present invention is able to maintain its adhesive strength in the presence of water, it can be preferably used for the underwater adhesion, but is not limited thereto. When the adhesive is used for the underwater adhesion, the active component of the adhesive may be preferably a coacervate, but is not limited thereto. For example, the adhesive of the present invention may be used as an environment-friendly adhesive for maintenance and repair of underwater structures, and more preferably used to repair the crack of swimming pool, bathtub, and vessel. Also, the adhesive of the present invention may be used as a medical adhesive, more preferably, as a soft (connective) tissue adhesive (e.g., as a skin adhesive to replace sutures and staples for closure of certain lacerations and/or incisions) and as a hard (calcified) tissue adhesive (e.g., as a bone or dental adhesive) (see <Example 4>).

The adhesive of the present invention can be used to be applied to a substrate selected from the group consisting of plastics, glasses, metals, and polymer resins. That is, it can be used to adhere or fix the substrate. The mode of use follows the general mode of adhesive use, and the typical mode is coating.

In particular, the adhesive of the present invention may be applied to a biological specimen, and the biological specimen refers to any animal or plant categorized as a biological organism and any part derived from such animal or plant. For example, it refers to cells, tissues, organs, RNAs, DNAs, proteins, peptides, polynucleotides, hormones, lipids, and compounds, but is not limited thereto. When it is applied to a biological specimen, the detailed mode and amount of usage and formulation of the adhesive of the present invention may follow commercially available CELL-TAK™ (polyphenolic proteins produced by the mussel *Mytilus edulis*, BD Biosciences, Two Oak Park, Bedford, Mass., USA). For example, the adhesive of the present invention may be a soluble, water-soluble, or insoluble formulation, and it may be used in an amount of 0.01 to 100 ug/cm$^2$ for a substrate, but is not limited thereto.

Examples of application of the adhesive of the present invention are as follows, but not limited thereto: (1) adhesion of substrates under water (fresh or salt water); (2) orthopedic treatments such as treatment of bone, ligament, tendon, meniscus, and muscle, and implant of artificial materials; (3) treatment of perforations, lacerations, and cuts, and ophthalmic attachments such as corneal implants and artificial corneal implants; (4) dental attachments such as holding retainers, bridges, or crowns in place, securing loose teeth, repairing broken teeth, and holding fillers in place; (5) surgical treatments such as attachment of blood vessels, attachment of cellular tissue, artificial material implants, and closure of wounds; (6) plant attachments such as bonding of transplanted parts and wound healing; (7) drugs, hormones, biological factors, medications, physiological or metabolic monitoring equipment, antibiotics, and cell transplant (see: U.S. Pat. No. 5,015,677).

In the present invention, the adhesive strength of the above adhesive can be adjusted by treating with a substance selected from the group consisting of surfactants, oxidants, crosslinking agents, and fillers, or by controlling the concentration of the coacervate which is an active component of the adhesive (see: U.S. Pat. No. 5,015,677). The oxidants, surfactants, crosslinking agents, and fillers are the same as described above.

The coacervate prepared by mixing the mussel adhesive protein or the mutant thereof and the anionic polymer is able to effectively deliver bioactive materials.

In one embodiment of the present invention, the coacervate is prepared by mixing the mussel adhesive protein or the mutant thereof with hyaluronic acid or heparin, and more preferably the coacervate is prepared by mixing the mussel adhesive protein consisting of the polypeptide of SEQ ID NO. 1 or 3 or the mutant of SEQ ID NO. 2 with hyaluronic acid or heparin, and then red pepper seed oil instead of a bioactive material is added and mixed therewith. As a result, it can be seen that the coacervate form a layer surrounding the red pepper seed oil (see (<Example 2>).

Therefore, the composition for delivering bioactive materials of the present invention is characterized by including the coacervate prepared by mixing the mussel adhesive protein or the mutant thereof with an anionic polymer.

The composition for delivering bioactive materials of the present invention may be preferably in a form of a pharmaceutical composition, but is not limited thereto.

The composition for delivering bioactive materials of the present invention may preferably include 0.0001 to 50% by weight of the coacervate, based on the total weight of the composition, but is not limited thereto. The composition of the present invention may further include one or more active components showing an identical or similar function, in addition to the above active component.

For administration, the composition for delivering bioactive materials of the present invention may be prepared by further including one or more pharmaceutically acceptable carriers in addition to the above described coacervate. The pharmaceutically acceptable carriers may include a saline solution, sterile water, a Ringer's solution, a buffered saline solution, a dextrose solution, a maltodextrin solution, glycerol, ethanol, liposome and a mixture of one or more thereof. If necessary, other conventional additives, such as antioxidants, buffers and bacteriostatic agents may be added. Moreover, diluents, dispersants, surfactants, binders and lubricants may be added so as to formulate it into injectable formulations, such as aqueous solutions, suspensions and emulsions, pills, capsules, granules and tablets. The carriers may be bound with target-specific antibodies or other ligands so as to have a function of targeting a specific organ. Furthermore, the composition may be preferably formulated depending on particular diseases or its components using a suitable method in the relevant field of art or the method described in Remington's Pharmaceutical Science (latest edition, Mack Publishing Company, Easton Pa.

The composition for delivering bioactive materials including the coacervate may be administered into the body via the intravenous, intraperitoneal, intramuscular, subcutaneous, intradermal, intranasal, mucosal, inhalation and oral route. The administration dose may vary depending on the subject's weight, age, sex, general health condition, and diet, administration time, administration route, secretion ratio, and severity of diseases. It is administered at a daily dose of approximately 0.1 to 100 mg/kg, and preferably 0.5 to 10 mg/kg once or several times a day.

Meanwhile, a delivery vehicle for bioactive materials of the present invention is characterized in that (a) the coacervate and the bioactive material are included, and (b) the bioactive material is encapsulated inside the coacervate.

The coacervate may be preferably a coacervate, but is not limited thereto.

The delivery vehicle for bioactive materials may be preferably a microcapsule, but is not limited thereto.

As described above, the coacervate may be prepared by mixing the mussel adhesive protein or the mutant thereof with an anionic polymer at pH 2.0 to pH 10.0 and a weight ratio of 1:0.01 to 1:10.

The coacervate forms a layer surrounding a bioactive material, for example, red pepper seed oil, thereby effectively encapsulating the bioactive material. Thus, a microcapsule can be formed as a delivery vehicle for bioactive materials. Moreover, the delivery vehicle maintains its shape even for a long period of time (see <Example 2>).

The formed delivery vehicle for bioactive materials may preferably have a diameter of 1 to 50 um, but is not limited thereto.

The delivery vehicle for bioactive materials of the present invention is able to encapsulate any hydrophobic or hydrophilic bioactive material inside the coacervate. Thus, a hydrophobic or hydrophilic bioactive material can be effectively encapsulated so as to achieve the effective delivery thereof. The bioactive material may be preferably encapsulated inside the coacervate in a dispersion form or in a core form, but is not limited thereto. The encapsulation refers to an enclosure of the bioactive material by forming a layer surrounding the bioactive material.

The delivery vehicle for bioactive materials of the present invention may be used as an active component of a pharmaceutical composition, as described above.

Meanwhile, a method for preparing the delivery vehicle for bioactive materials of the present invention is characterized by including the steps of (a) mixing the mussel adhesive protein or the mutant thereof with an anionic polymer and a bioactive material, and (b) forming a layer surrounding the bioactive material by a coacervate that is formed by the mussel adhesive protein or the mutant thereof and the anionic polymer.

In step (a), the mixing means that the mussel adhesive protein or the mutant thereof is simultaneously mixed with the anionic polymer and the bioactive material, or more preferably that the bioactive material is mixed with a solution dissolving any one of the mussel adhesive protein or the mutant thereof and the anionic polymer, and then any remaining one of the mussel adhesive protein or the mutant thereof and the anionic polymer is added in order to induce the coacervation.

Specifically, a mixing ratio of the mussel adhesive protein or the mutant thereof and the anionic polymer is the same as described above. Further, the mussel adhesive protein or the mutant thereof and the anionic polymer may be preferably mixed at an amount of 0.0001 to 50% by weight in a solvent with the optimal pH as described above, but is not limited thereto. Furthermore, when the mixing is performed in step (a), the bioactive material is preferably mixed in a volume of 1 to 20% (v/v), and more preferably 0.1 to 2% (v/v), based on the volume of the solvent with the optimal pH as described above, but is not limited thereto.

The type, optimal pH, and optimal temperature of the solvent used for the preparation of the delivery vehicle for bioactive materials are the same as in the aforementioned conditions for the effective coacervation.

Specifically, the optimal solvent may be preferably an aqueous solvent, and more preferably a phosphate aqueous solution or an acetic acid aqueous solution, still more preferably an acetic acid aqueous solution, yet still more preferably a 0.1% to 10% acetic acid aqueous solution, and most preferably a 0.5 to 8% acetic acid aqueous solution, but is not limited thereto.

The optimal pH may be preferably pH 2.0 to pH 10.0, more preferably pH 2.0 to pH 6.0, and most preferably pH 2.5 to pH 5.5, but is not limited thereto. If the pH is not within the above range, coacervation may not occur, or polymer deformation may occur, and thus the delivery vehicle for bioactive materials cannot be effectively formed.

Further, the optimal temperature may be 4 to 100° C., and preferably 10 to 60° C. If the temperature is not within the above range, coacervation may not occur, or polymer deformation may occur.

Meanwhile, a method for preparing the coacervate of the present invention is characterized by including the step of mixing the mussel adhesive protein or the mutant thereof with an anionic polymer at pH 2.0 to pH 10.0 and a weight ratio of 1:0.01 to 1:10.

The coacervate of the present invention may be preferably prepared in an aqueous solvent, and more preferably in a phosphate aqueous solution or an acetic acid aqueous solution, still more preferably in an acetic acid aqueous solution, yet still more preferably in a 0.1% to 10% acetic acid aqueous solution, and most preferably in a 0.5 to 8% acetic acid aqueous solution, but is not limited thereto.

If the coacervate of the present invention is prepared in the above solvent, the optimal pH may be pH 2.0 to pH 10.0, more preferably pH 2.0 to pH 6.0, and most preferably pH 2.5 to pH 5.5. If the pH is not within the above range, coacervation may not occur, or polymer deformation may occur. Further, the optimal temperature may be 4 to 100° C., and preferably 10 to 60° C. If the temperature is not within the above range, coacervation may not occur, or polymer deformation may occur.

The mussel adhesive protein or the mutant thereof and the anionic polymer may be preferably added to the solvent in a volume of 0.001 to 100% (w/v), and more preferably 0.01 to 30% (w/v), based on the total volume of the solvent, but is not limited thereto.

The coacervate of the present invention may be preferably prepared by mixing the mussel adhesive protein or the mutant thereof with the anionic polymer at a weight ratio of 1:0.01 to 1:10, more preferably 1:0.25 to 1:2.5, and most preferably 1:0.25 to 1:2.33, but is not limited thereto. If the mixing ratio is not within the above range, coacervation may not occur effectively.

Meanwhile, the present invention provides the use of the coacervate of the present invention in adhesion, and the description thereof is the same as described above. In particular, the coacervate of the present invention may be used in the preparation of adhesives.

Further, the present invention provides a method for using the coacervate of the present invention in adhesion, including the steps of (a) preparing the coacervate of the present invention and (b) adhering the coacervate to a substrate, and the description thereof is the same as described above.

Further, the present invention provides the use of the coacervate of the present invention for the delivery of bioactive materials, and the description thereof is the same as described above.

Further, the present invention provides a method for using the coacervate of the present invention for the delivery of bioactive materials, including the steps of (a) preparing the coacervate of the present invention and (b) encapsulating a bioactive material inside the coacervate, and the description thereof is the same as described above.

Further, the present invention provides the use of the coacervate of the present invention in the preparation of a delivery vehicle for bioactive materials, and the description thereof is the same as described above.

Further, the present invention provides a method for using the coacervate of the present invention in the preparation of a delivery vehicle for bioactive materials, including the steps of preparing the coacervate of the present invention and (b) encapsulating the bioactive material inside the coacervate, and the description thereof is the same as described above.

Advantageous Effects

In the present invention, a coacervate prepared by mixing a mussel adhesive protein and an anionic polymer shows a very excellent adhesive strength to various substrates such as cells or metals, and is able to maintain its adhesive strength in the presence of water or under water, thereby being effectively used as an adhesive. Moreover, it has an activity capable of encapsulating bioactive materials, thereby being effectively used as an active component of a composition for delivering bioactive materials.

DESCRIPTION OF DRAWINGS

The patent or application file contains at least one drawing executed in color. Copies of this patent or patent application publication with color drawing(s) will be provided by the Office upon request and payment of the necessary fee.

MODE FOR INVENTION

Figure 1:
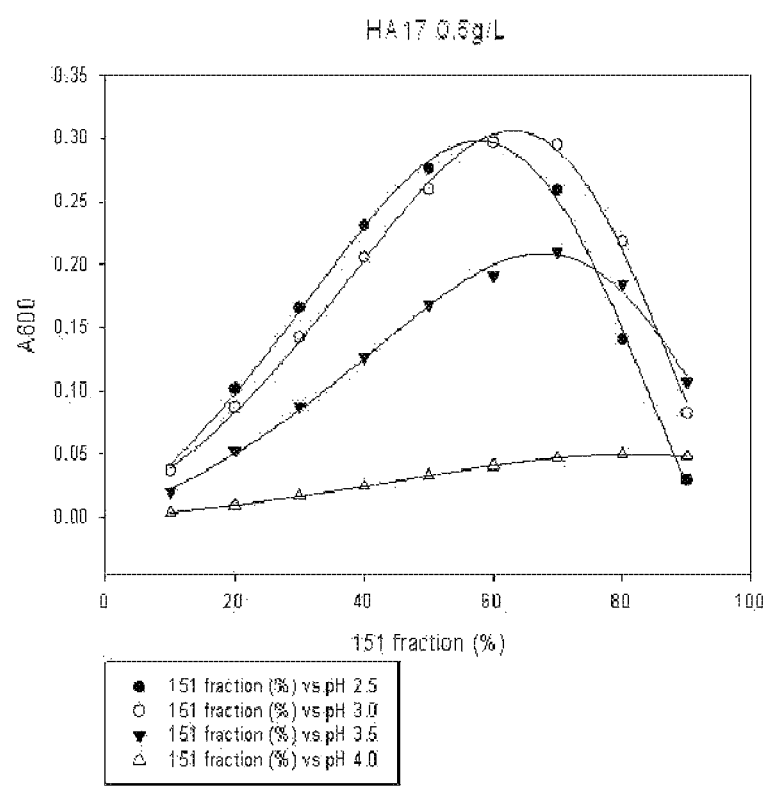
FIG. 1 is the result of measuring changes in absorbance when a mussel adhesive protein, fp-151 is mixed with an anionic polymer, hyaluronic acid (17 kDa) at a variety of pH values and ratios.

Hereinafter, the present invention will be described in detail with reference to Examples.

However, the following Examples are for illustrative purposes only, and the invention is not intended to be limited by the following Examples.

Reference Example 1

Preparation of Mussel Adhesive Protein

<1-1> Preparation of Mussel Adhesive Protein, fp-151

A mussel adhesive protein, fp-151 was prepared as follows. An fp-1 mutant consisting of six repeats of decapeptide was synthesized, in order to express the decapeptide in *E. coli*, in which the decapeptide consists of 10 amino acids occurring 80 times in a natural mussel adhesive protein fp-1. The Mgfp-5 gene (Genbank No. AAS00463 or AY521220) was inserted between two fp-1 mutants, and expressed in *E. coli* to produce fp-151 (D. S. Hwang et. al., Biomaterials 28, 3560-3568, 2007).

Specifically, the fp-1 mutant (hereinafter, referred to as 6xAKPSYPPTYK) consisting of six repeats of AKPSYPP-TYK represented by SEQ ID NO. 4 in the amino acid sequence of fp-1 (Genbank No. Q27409 or 523760) was prepared, and 6xAKPSYPPTYK was linked at the N-terminus of Mgfp-5, and 6xAKPSYPPTYK was linked at the C-terminus of Mgfp-5 so as to prepare fp-151 of SEQ ID NO. 1.

<1-2> Preparation of Mussel Adhesive Protein, fp-151-RGD

The GRGDSP sequence selected from fibronectin-derived RGD sequences was added to the C-terminus of fp-151 of <Example 1-1> so as to prepare fp-151-RGD of SEQ ID NO. 2.

<1-3> Preparation of Mussel Adhesive Protein, fp-131

A mussel adhesive protein, fp-131 was also prepared in the same manner as in the preparation of fp-151 of <Example 1-1>. That is, a gene of the natural mussel adhesive protein Mgfp-3A (Genbank No. BAB16314 or AB049579) was inserted between two fp-1 mutants, and expressed in *E. coli*.

Specifically, the fp-1 mutant represented by SEQ ID NO. 7 (hereinafter, referred to as 6xAKPSYPPTYK) consisting of six repeats of AKPSYPPTYK represented by SEQ ID NO. 6 in the amino acid sequence of fp-1 (Genbank No. Q27409 or 523760) was prepared, and 6xAKPSYPPTYK was linked at the N-terminus of Mgfp-3, and 6xAKPSYPPTYK was linked at the C-terminus of Mgfp-3 so as to prepare fp-131 of SEQ ID NO. 3.

<1-4> Preparation of Mussel Adhesive Protein, fp-5

A mussel adhesive protein, fp-5 was prepared by expressing a gene of the natural mussel adhesive protein Mgfp-5 (Genbank No. AAS00463 or AY521220) in *E. coli* (D. S. Hwang et. al., applied and environmental microbiology, 3352-3359, 2004).

Example 1

Coacervate Formation Using Mussel Adhesive Protein

Coacervate is a colloid produced by mixing an anionic polymer electrolyte and a cationic polymer electrolyte at a particular ratio under particular pH condition. When a coacervate is formed, absorbance of a solution increases. Thus, absorbance is usually measured to examine whether coacervation occurs (V. Ducel et. al., Colloids and Surfaces a-Physicochemical and Engineering Aspects, 232, 239-247, 2004). In the following Examples, each of the mussel adhesive proteins prepared in Reference Examples is mixed with an anionic polymer electrolyte, and then it is examined whether coacervation occurs.

<1-1> Coacervate Formation Using Mussel Adhesive Protein fp-151 and Hyaluronic Acid (17 kDa)

It was examined whether coacervates were formed by mixing the mussel adhesive protein fp-151 prepared in <Reference Example 1-1> with an anionic polymer electrolyte, hyaluronic acid.

Specifically, hyaluronic acid (Lifcore Biomedical; Minnesota, USA) having a molecular weight of 17 kDa was dissolved in 5% acetic acid (pH adjusted with sodium hydroxide) at a concentration of 0.05% (w/v). The mussel adhesive protein fp-151 dissolved in the same solution was mixed therewith while its ratio in the solvent (mussel adhesive protein and hyaluronic acid) was increased with a ratio change of 10% (w/w). After mixing, absorbance at a wavelength of 600 nm was measured using a UV-spectrophotometer (Optizen 3220UVbio, Mecasys, Daejeon, Korea), and the results are shown in FIG. 1.

As shown in FIG. 1, it was found that coacervates were most effectively formed at pH 2.5 and a weight ratio of fp-151 to hyaluronic acid (17 kDa) of 58:42, at pH 3.0 and a weight ratio of 63:37, and at pH 3.5 and a weight ratio of 68:32.

Figure 2:
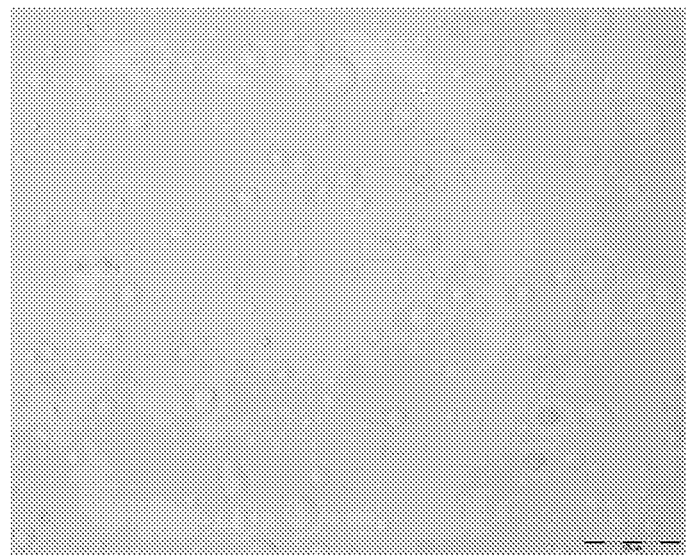
FIG. 2 is the result of coacervation when a mussel adhesive protein, fp-151 is mixed with hyaluronic acid (17 kDa) in an acetic acid solution of pH 2.5 at a ratio of 60:40.

Further, microscopy was carried out to examine whether the increased absorbance was attributed to coacervation, and the results are shown in FIG. 2.

As shown in FIG. 2, spheres having a size of approximately 10 μm were found to be formed, indicating coacervates produced by the mussel adhesive protein fp-151 and hyaluronic acid (17 kDa).

<1-2> Coacervate Formation Using Mussel Adhesive Protein fp-131 and Hyaluronic Acid (17 kDa)

Coacervate formation was examined in the same manner as in <Example 1-1>, except for using the mussel adhesive protein fp-131 prepared in <Reference Example 1-3>. The results are shown in FIGS. 3 and 4.

Figure 3:
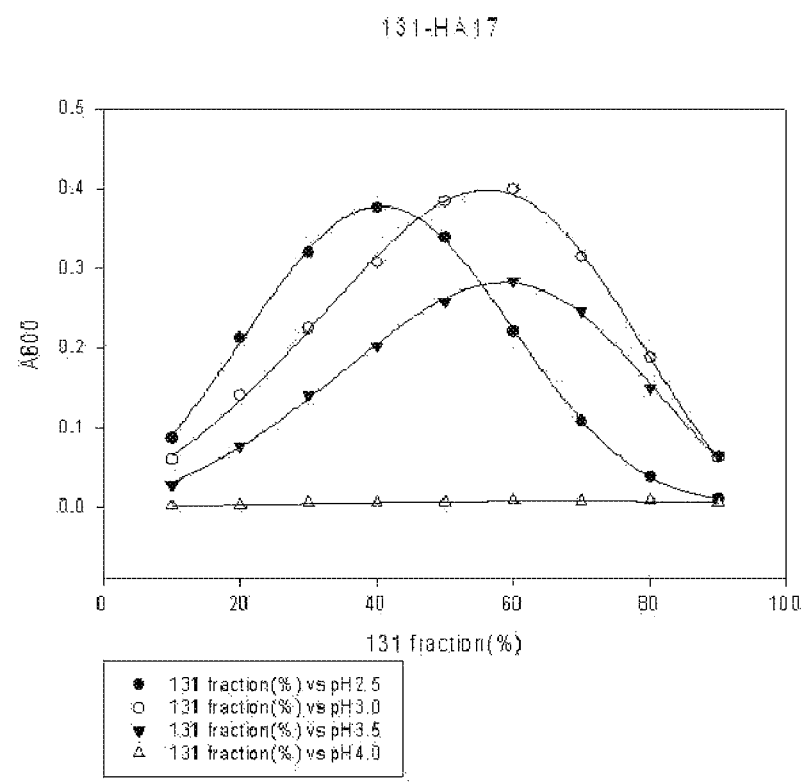
FIG. 3 is the result of measuring changes in absorbance when a mussel adhesive protein, fp-131 is mixed with hyaluronic acid (17 kDa) at a variety of pH values and ratios.
Figure 4:
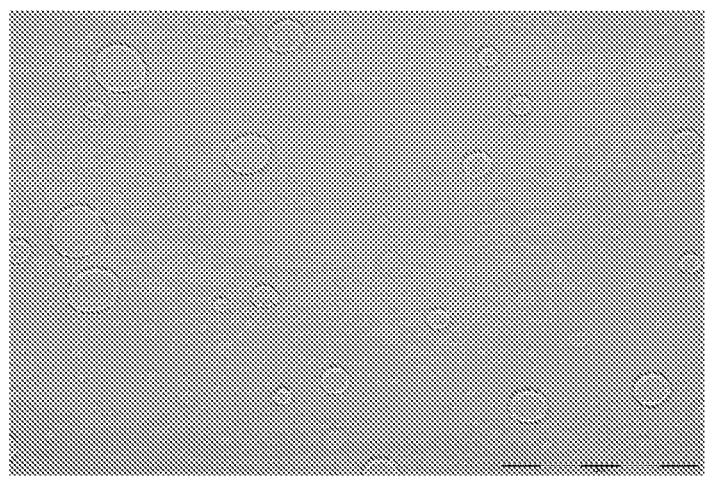
FIG. 4 is the result of coacervation when a mussel adhesive protein, fp-131 is mixed with hyaluronic acid (17 kDa) in an acetic acid solution of pH 2.5 at a ratio of 60:40.

As shown in FIGS. 3 and 4, it was found that coacervates were most effectively formed at pH 2.5 and a weight ratio of fp-131 to hyaluronic acid (17 kDa) of 41:59, at pH 3.0 and a weight ratio of 56:44, and at pH 3.5 and a weight ratio of 59:41.

<1-3> Coacervate Formation Using Mussel Adhesive Protein fp-151-RGD and Hyaluronic Acid (17 kDa)

Coacervate formation was examined in the same manner as in <Example 1-1>, except for using the mussel adhesive protein fp-151-RGD prepared in <Reference Example 1-2>. The results are shown in FIGS. 5 and 6.

Figure 5:
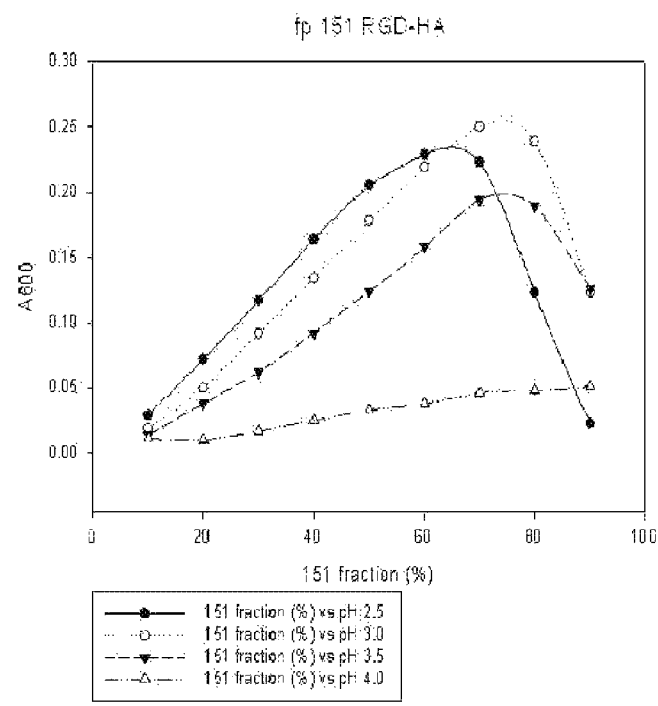
FIG. 5 is the result of measuring changes in absorbance when a mussel adhesive protein, fp-151-RGD is mixed with hyaluronic acid (17 kDa) at a variety of pH values and ratios.
Figure 6:
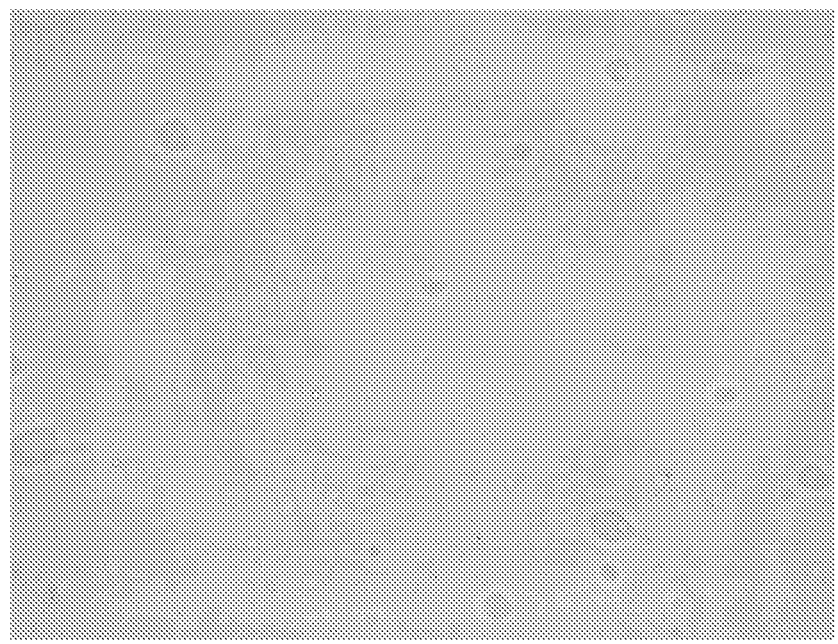
FIG. 6 is the result of coacervation when a mussel adhesive protein, fp-151-RGD is mixed with hyaluronic acid (17 kDa) in an acetic acid solution of pH 2.5 at a ratio of 60:40.

As shown in FIGS. 5 and 6, it was found that coacervates were most effectively formed at pH 2.5 and a weight ratio of fp-151-RGD to hyaluronic acid (17 kDa) of 60:40, at pH 3.0 and a weight ratio of 70:30, and at pH 3.5 and a weight ratio of 73:27. In particular, absorbance was more greatly increased by using fp-151-RGD than fp-151, indicating that coacervates were more effectively formed.

<1-4> Coacervate Formation Using Mussel Adhesive Protein fp-151 and Hyaluronic Acid (35 kDa)

Coacervate formation was examined in the same manner as in <Example 1-1>, except for using hyaluronic acid (35 kDa). The results are shown in FIGS. 7 and 8.

Figure 7:
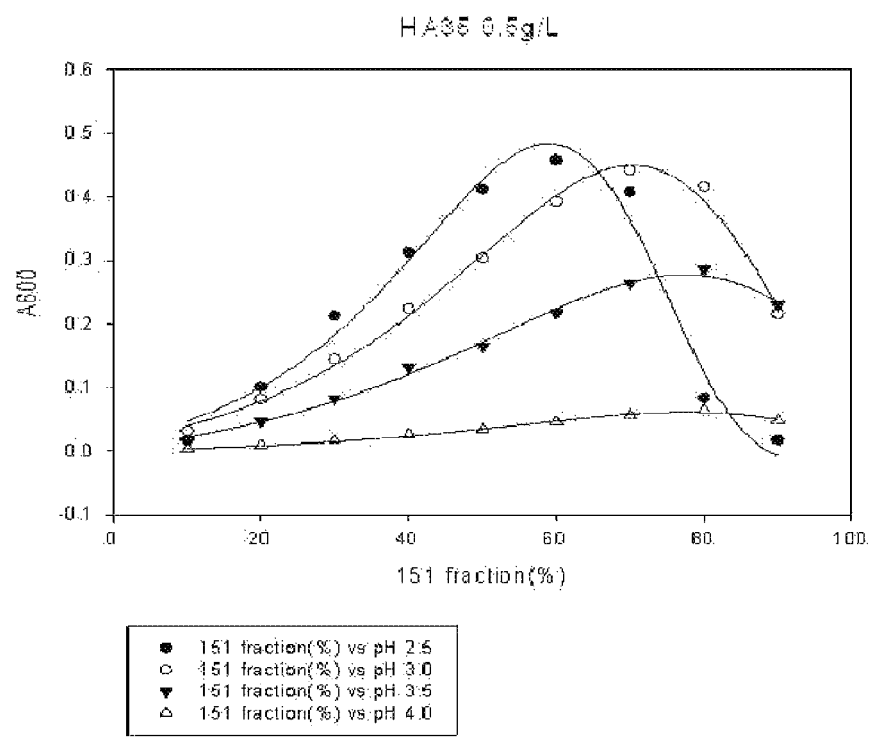
FIG. 7 is the result of measuring changes in absorbance when a mussel adhesive protein, fp-151 is mixed with hyaluronic acid (35 kDa) at a variety of pH values and ratios.
Figure 8:
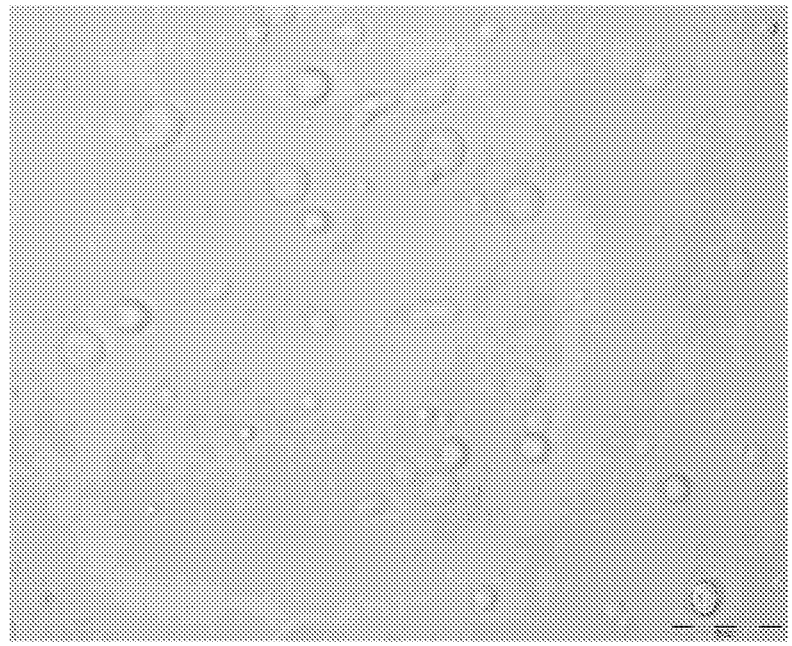
FIG. 8 is the result of coacervation when a mussel adhesive protein, fp-151 is mixed with hyaluronic acid (35 kDa) in an acetic acid solution of pH 2.5 at a ratio of 60:40.

As shown in FIGS. 7 and 8, it was found that coacervates were most effectively formed at pH 2.5 and a weight ratio of fp-151 to hyaluronic acid (35 kDa) of 59:41, at pH 3.0 and a weight ratio of 70:30, and at pH 3.5 and a weight ratio of 77:27. In particular, absorbance was more greatly increased by using 35 kDa hyaluronic acid than 17 kDa hyaluronic acid, indicating that coacervates were more effectively formed.

<1-5> Coacervate Formation Using Mussel Adhesive Protein fp-151 and Hyaluronic Acid (59 kDa)

Coacervate formation was examined in the same manner as in <Example 1-1>, except for using hyaluronic acid (59 kDa). The results are shown in FIGS. 9 and 10.

Figure 9:
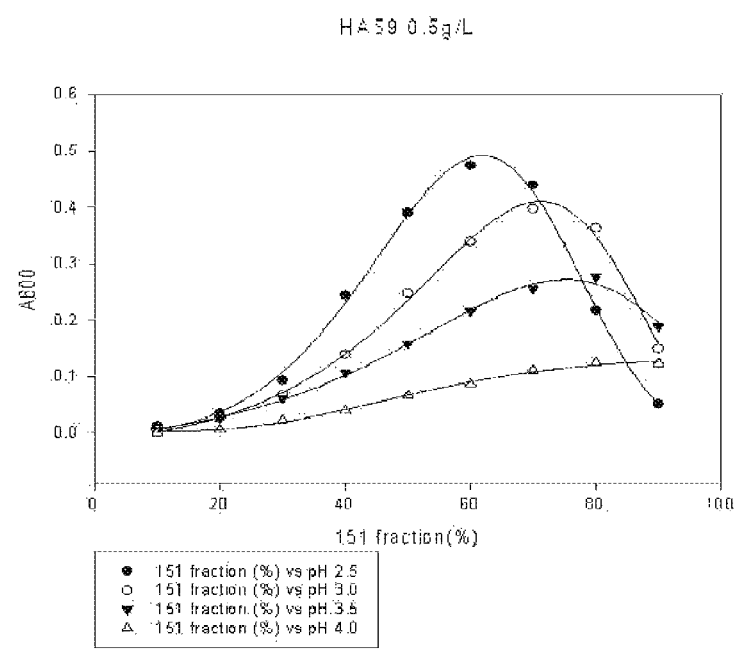
FIG. 9 is the result of measuring changes in absorbance when a mussel adhesive protein, fp-151 is mixed with hyaluronic acid (59 kDa) at a variety of pH values and ratios.
Figure 10:
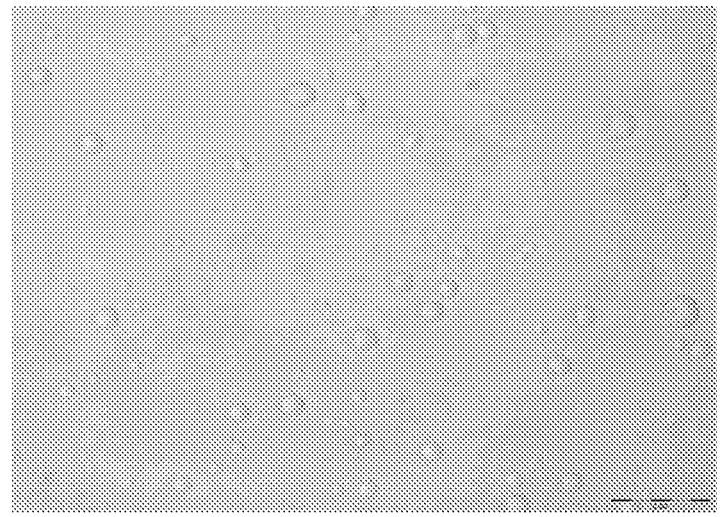
FIG. 10 is the result of coacervation when a mussel adhesive protein, fp-151 is mixed with hyaluronic acid (59 kDa) in an acetic acid solution of pH 2.5 at a ratio of 60:40.

As shown in FIGS. 9 and 10, it was found that coacervates were most effectively formed at pH 2.5 and a weight ratio of fp-151 to hyaluronic acid (59 kDa) of 62:38, at pH 3.0 and a weight ratio of 71:29, and at pH 3.5 and a weight ratio of 75:25. In particular, absorbance was more greatly increased by using 59 kDa hyaluronic acid than 17 kDa hyaluronic acid, indicating that coacervates were more effectively formed.

<1-6> Coacervate Formation Using Mussel Adhesive Protein fp-131 and Ferredoxin

Figure 17:
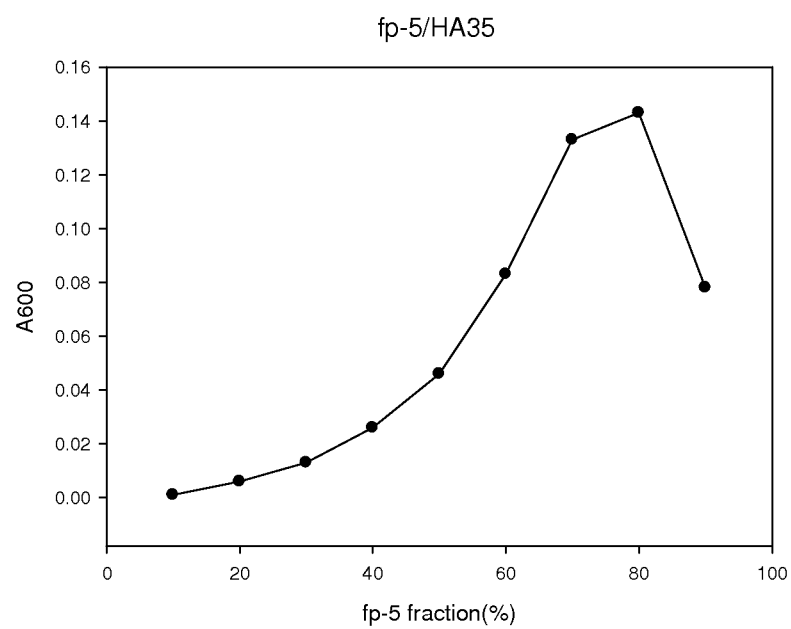
FIG. 17 is the result of measuring changes in absorbance when a mussel adhesive protein, fp-5 is mixed with hyaluronic acid (35 kDa) at pH 4.6.

Coacervate formation was examined at pH 4.5 and a weight ratio of fp-131 to ferredoxin of 70:30 in the same manner as in <Example 1-1>, except for using fp-131 prepared in <Reference Example 1-3> as the mussel adhesive protein. The results are shown in FIG. 17.

Figure 15:
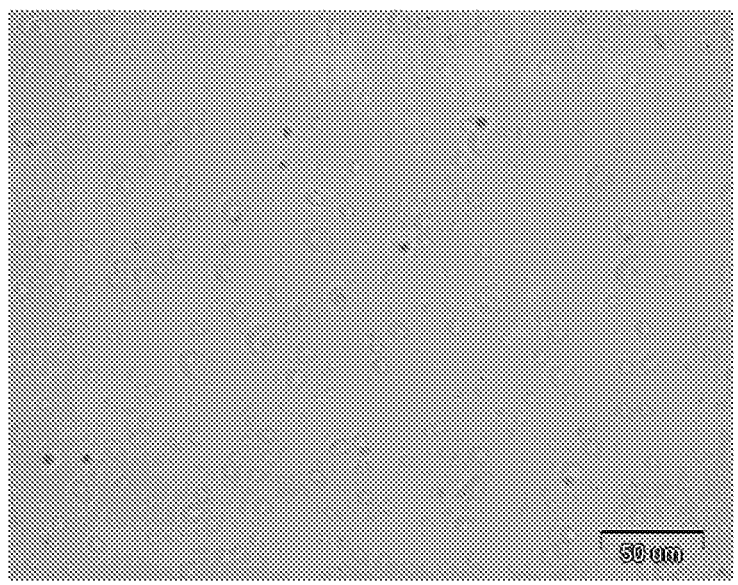
FIG. 15 is the result of coacervation when a mussel adhesive protein, fp-131 is mixed with ferredoxin in an acetic acid solution of pH 4.5 at a ratio of 70:30.

As shown in FIG. 15, it was found that coacervates were formed by using the mussel adhesive protein fp-131 and ferredoxin.

<1-7> Coacervate Formation Using Mussel Adhesive Protein fp-131 and Hyaluronic Acid (35 kDa)

Figure 11:
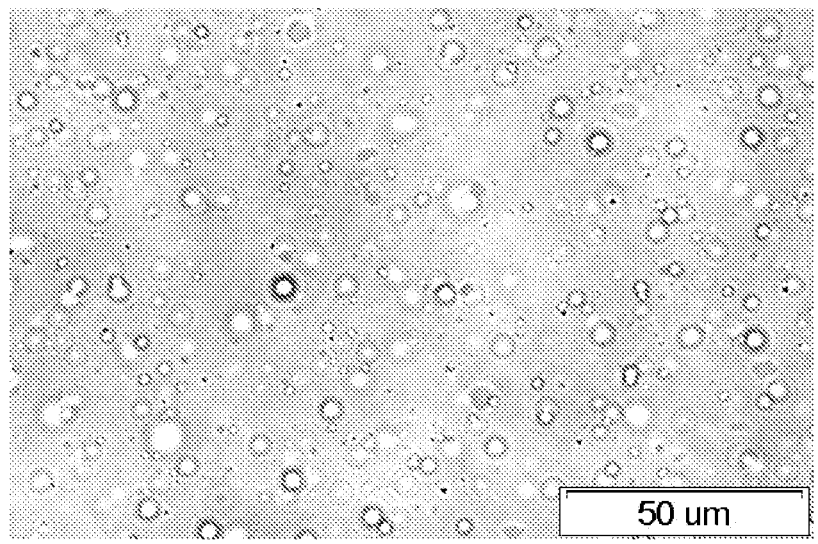
FIG. 11 is the result of coacervation when a mussel adhesive protein, fp-131 is mixed with hyaluronic acid (35 kDa) in an acetic acid solution of pH 3.8 at a ratio of 80:20.

Coacervate formation was examined at pH 3.8 and a weight ratio of fp-131 to hyaluronic acid (35 kDa) of 80:20 in the same manner as in <Example 1-5>, except for using the mussel adhesive protein fp-131 prepared in <Reference Example 1-3>. The results are shown in FIG. 11.

<1-8> Coacervate Formation Using Mussel Adhesive Protein fp-131 and Hyaluronic Acid (59 kDa)

Figure 12:
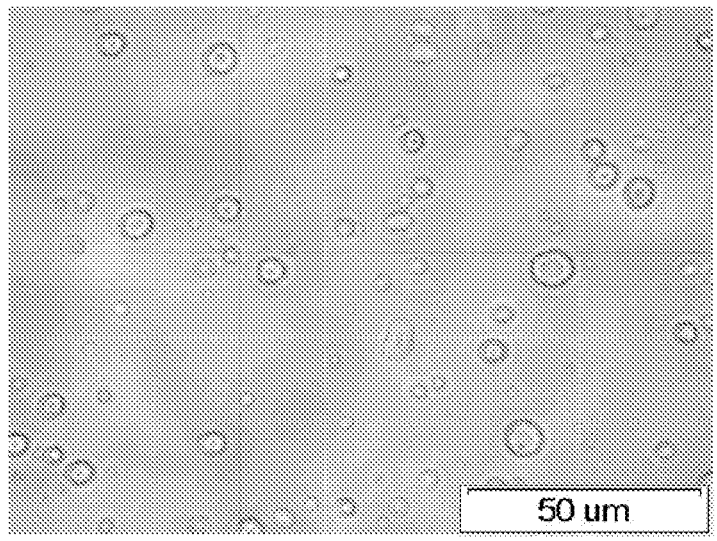
FIG. 12 is the result of coacervation when a mussel adhesive protein, fp-131 is mixed with hyaluronic acid (59 kDa) in an acetic acid solution of pH 3.8 at a ratio of 80:20.

Coacervate formation was examined at pH 3.8 and a weight ratio of fp-131 to hyaluronic acid (59 kDa) of 80:20 in the same manner as in <Example 1-6>, except for using the mussel adhesive protein fp-131 prepared in <Reference Example 1-3>. The results are shown in FIG. 12.

<1-9> Coacervate Formation Using Mussel Adhesive Protein fp-151 and Heparin

Absorbances of heparin (sigma) and fp-151 were determined at pH 4.0, pH 5.0, and pH 5.5, respectively. Heparin was dissolved at a concentration of 0.02% (w/v) in 100 mM sodium acetate buffer at the above pH, and mixed with fp-151 dissolved in the same solution at mixing ratios of 10-90% with a ratio change of 10%. Then, absorbance was measured, and the results are shown in FIGS. 13 and 14.

Figure 13:
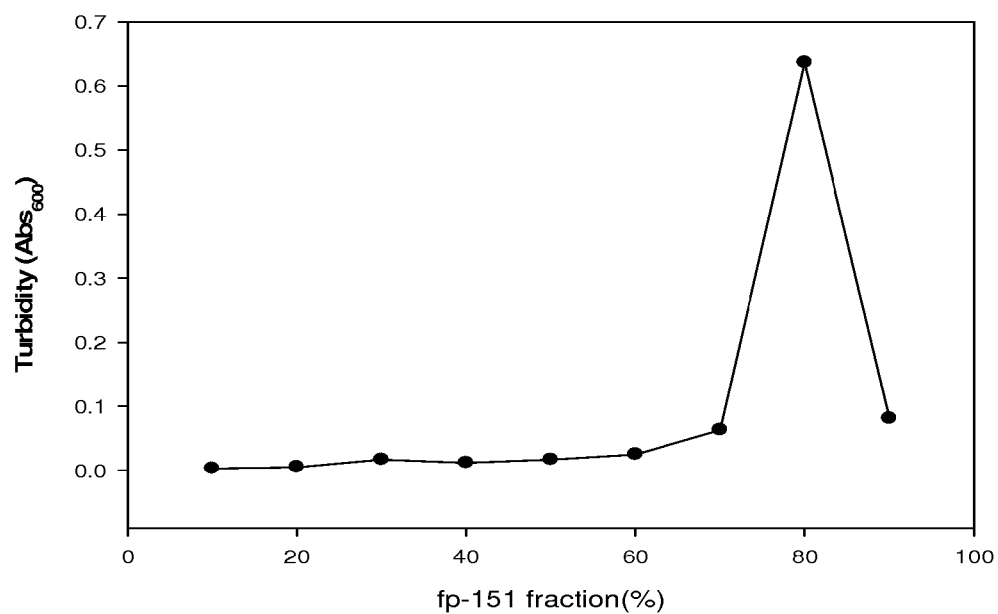
FIG. 13 is the result of measuring changes in absorbance when a mussel adhesive protein, fp-151 is mixed with heparin at a variety of pH values and ratios.
Figure 14:
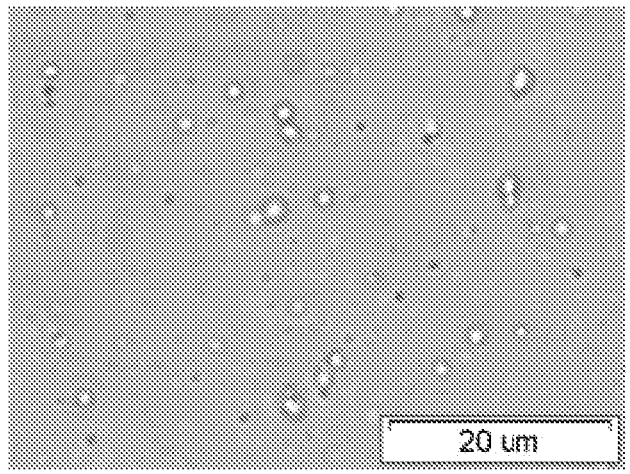
FIG. 14 is the result of coacervation when a mussel adhesive protein, fp-131 is mixed with heparin in acetic acid solutions with a variety of pH values at a ratio of 80:20.

As shown in FIGS. 13 and 14, the highest absorbance was observed at pH 5.0 and a weight ratio of fp-151 to heparin of 90:10, and coacervation was also observed as in FIG. 14.

<1-10> Coacervate Formation Using Mussel Adhesive Protein fp-5 and Hyaluronic Acid (35 kDa)

Coacervate formation was examined in the same manner as in <Example 1-4>, except for using the mussel adhesive protein fp-5 prepared in <Reference Example 1-4>. The results are shown in FIGS. 16 and 17.

Figure 16:
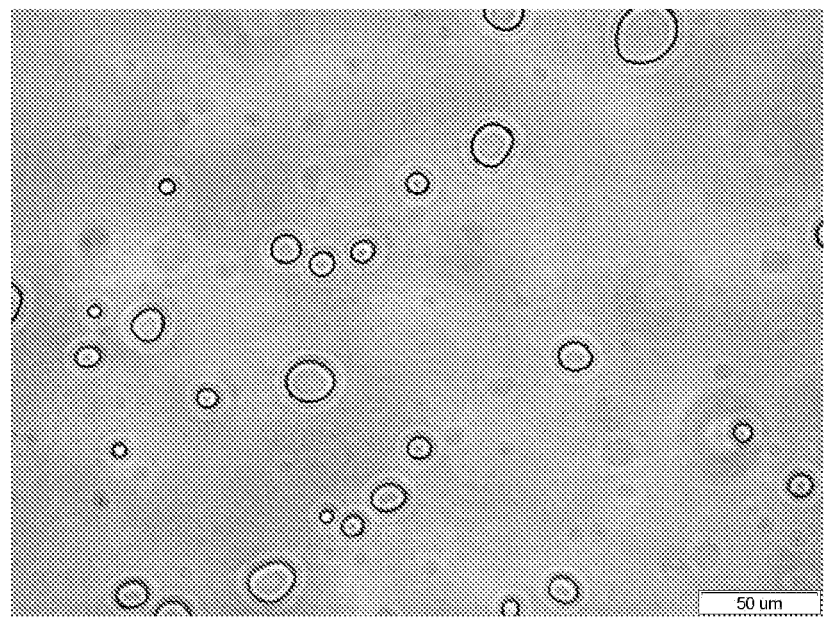
FIG. 16 is the result of coacervation when a mussel adhesive protein, fp-5 is mixed with hyaluronic acid (35 kDa) in an acetic acid solution of pH 4.6 at a ratio of 80:20.

As shown in FIGS. 16 and 17, the highest absorbance was observed at pH 4.6 and a weight ratio of fp-5 to hyaluronic acid (35 kDa) of 80:20.

Example 2

Microencapsulation Potential of Coacervate

<2-1> Microencapsulation Potential of Coacervate Formed by Mussel Adhesive Protein fp-151 and Hyaluronic Acid (35 kDa)

10 g/L of fp-151 was dissolved in 100 mM acetate buffer, of which pH was adjusted with sodium hydroxide to pH 3.8, and then red pepper seed oil was added thereto at a volume of 1%, based on the final volume. For emulsification, the mixture was stirred for 10 minutes. After stirring, hyaluronic acid (35 kDa) was added to the emulsion of red pepper seed oil at a weight ratio of fp-151 to hyaluronic acid of 8:2.

Figure 18:
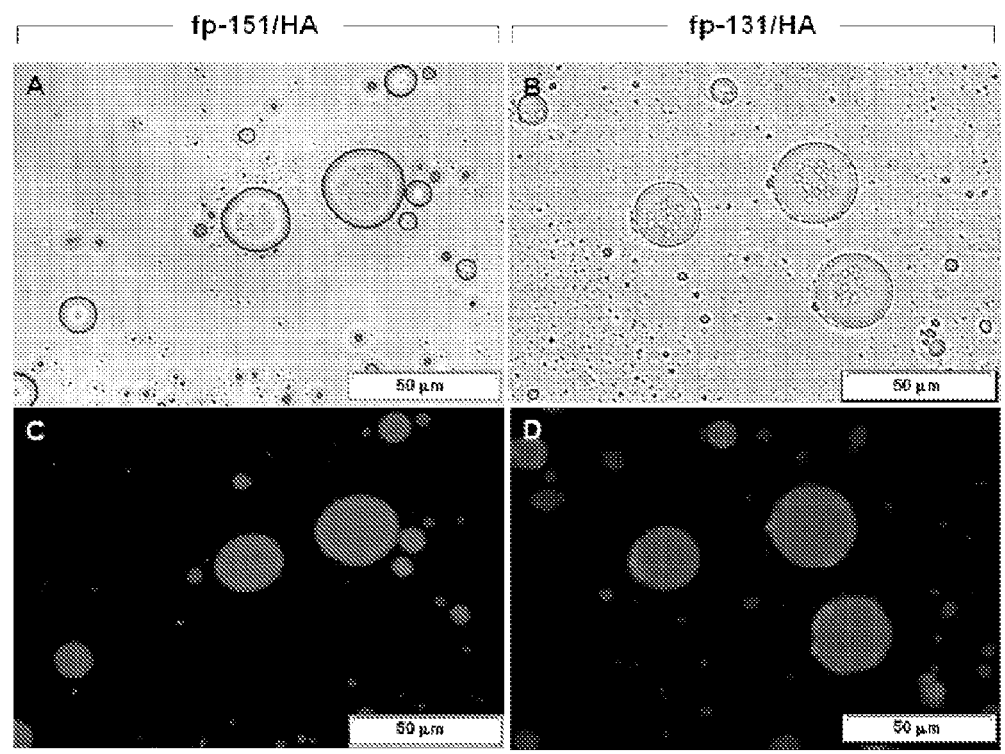
FIG. 18 is the result of encapsulating red pepper seed oil in a microcapsule using a coacervate prepared by using a mussel adhesive protein, fp-151 and hyaluronic acid (35 kDa) and a coacervate prepared by using a mussel adhesive protein fp-131 and hyaluronic acid (35 kDa)

Thereafter, for evaluation of microencapsulation potential, fluorescence emission of red pepper seed oil was analyzed by fluorescence microscopy (Olympus), and the results are shown in FIG. 18. It was also examined whether the microcapsules were maintained for at least 8 days, and the results are shown in FIG. 19.

Figure 19:
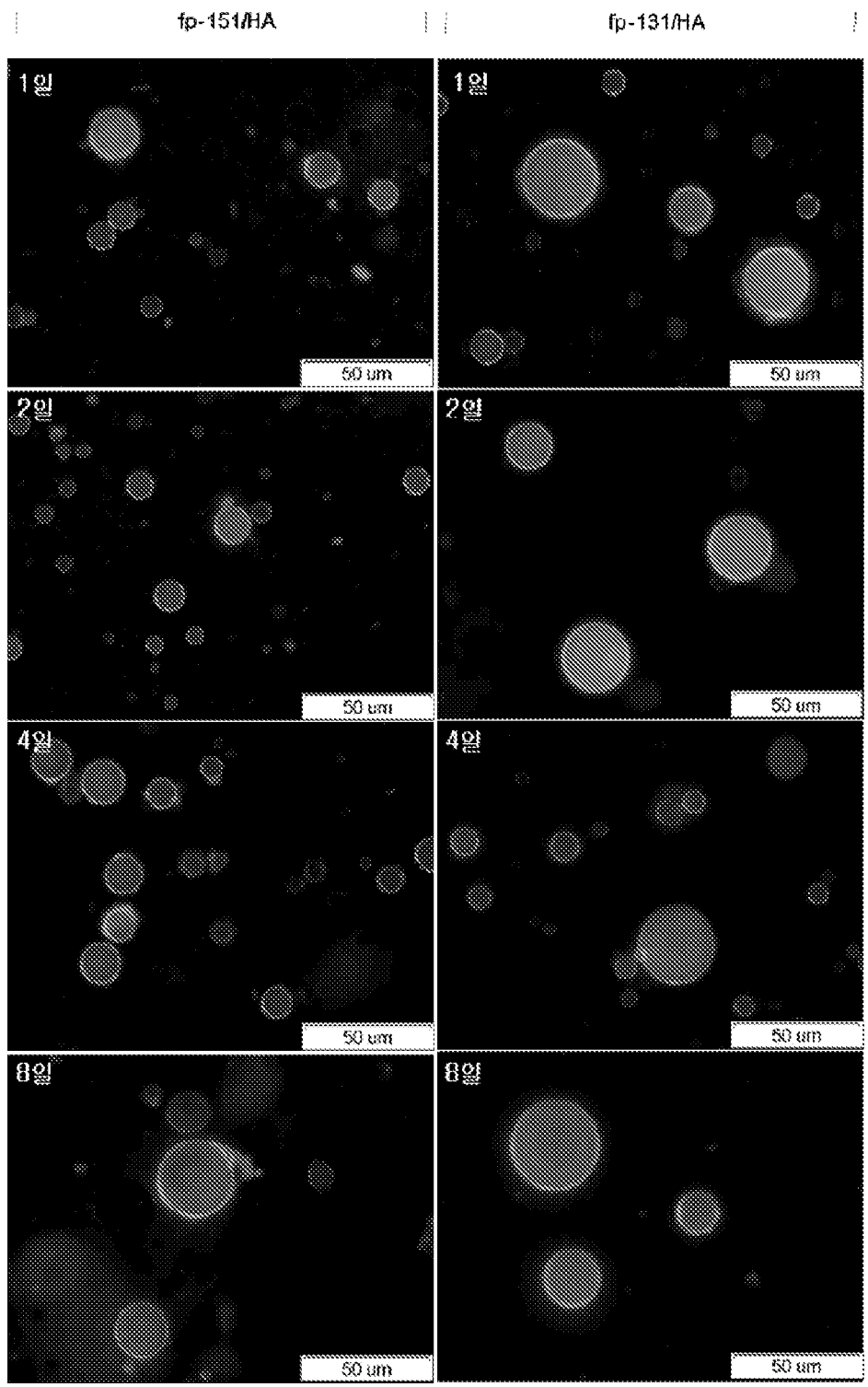
FIG. 19 is the result showing whether the microcapsules formed in FIG. 18 are maintained for 8 days.

As shown in FIGS. 18 and 19, it can be seen that the coacervates formed by the mussel adhesive protein and hyaluronic acid has a microencapsulation potential, and in particular, the formed microcapsules are maintained even after 8 days.

<2-2> Microencapsulation Potential of Coacervate Formed by Mussel Adhesive Protein fp-131 and Hyaluronic Acid (35 kDa)

Microencapsulation potential of the coacervates formed by the mussel adhesive protein fp-131 and hyaluronic acid (35 kDa) was examined in the same manner as in <Example 2-1>, except for using fp-131 as the mussel adhesive protein, and the results are shown in FIGS. 18 and 19.

As shown in FIGS. 18 and 19, it can be seen that the coacervates formed by the mussel adhesive protein and hyaluronic acid has a microencapsulation potential, and in particular, the formed microcapsules are maintained even after 8 days.

Figure 20:
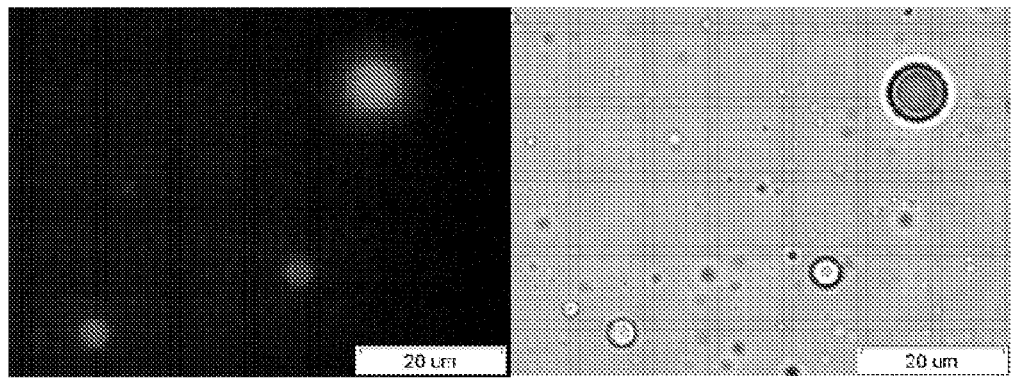
FIG. 20 is the result of encapsulating red pepper seed oil in a microcapsule using a coacervate prepared by using a mussel adhesive protein, fp-151 and heparin.

<2-3> Microencapsulation Potential of Coacervate Formed by Mussel Adhesive Protein fp-151 and Heparin Microencapsulation potential of the coacervates formed by the mussel adhesive protein fp-151 and heparin was examined in the same manner as in <Example 2-1>, except for using heparin instead of hyaluronic acid at a weight ratio of fp-151 to heparin of 9:1, and the results are shown in FIG. 20.

Example 3

Cell Adhesive Activity of Coacervate

<3-1> Cell Adhesive Activity of Coacervate Formed by Mussel Adhesive Protein fp-151 and Hyaluronic Acid (17 kDa)

An untreated 24-well culture plate was coated with the coacervate formed in <Example 1-1> to examine its cell adhesive activity. As a positive control, fp-151 and poly-L-lysine known to have the cell adhesive activity were used. With respect to the positive control group, the known precipitation method by sodium bicarbonate was used (Fulkerson, J. P. et al., (1990) Journal of Orthopaedic Research 8 (6), pp. 793-798, (1990)).

Specifically, *Drosophila* S2 cells (Invitrogen) used in this experiment were cultured in a 27° C. incubator using an insect cell culture medium M3 (Sigma) containing 10% IMS (insect medium supplement, Sigma), 1% antibiotic-antimycotic (Invitrogen), and µl/ml hygromycin (hyclone). The cells were diluted in the above culture medium at a density of $1\times10^5$ cells/ml, and then $5\times10^4$ cells were added to each well of a cell culture plate coated with the coacervates, followed by incubation for 1 hour. After cultivation, 3-(4,5-dimethylthiazol-2-yl)-2,5-diphenyltetrazolium bromide (MTT) assay was performed to quantify cell viability. First, to remove non-adhered cells after the cultivation, the plate was washed with PBS (phosphate buffered saline), and 300 µl of MTT solution was added to each well. MTT is reduced to MTT formazan in the mitochondria of living cells. After incubation with MTT solution for further 2 hours, MTT formazan was resolubilized by the addition of dimethyl sulfoxide (DMSO), and absorbance was measured at 570 nm using a spectrophotometer. The results are shown in FIG. 21.

Figure 21:
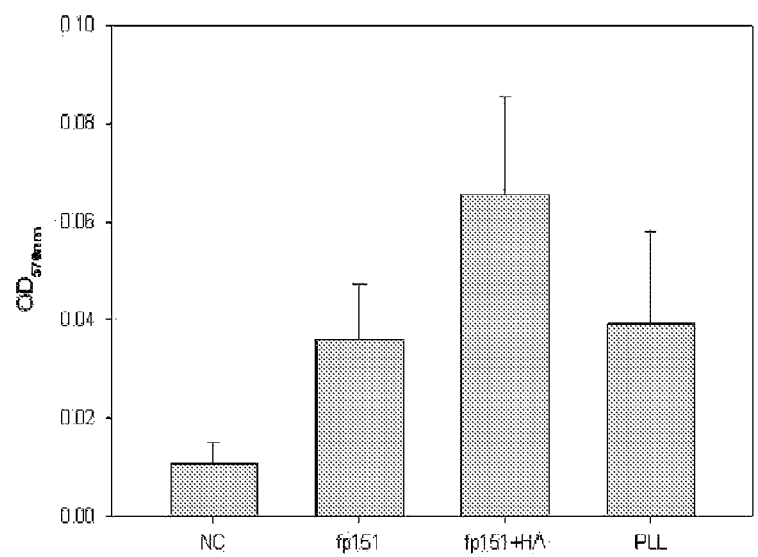
FIG. 21 is the result of performing cell adhesion, after a coacervate is prepared by using a mussel adhesive protein, fp-151 and hyaluronic acid (17 kDa) and the surface is coated therewith.

As shown in FIG. 21, coacervates formed by the mussel adhesive protein fp-151 and hyaluronic acid (17 kDa) showed excellent cell adhesive activity, compared to the positive control groups such as fp-151 and poly-L-lysine.

<3-2> Cell Adhesive Activity of Coacervate Formed by Mussel Adhesive Protein fp-151-RGD and Hyaluronic Acid (17 kDa)

Figure 22:
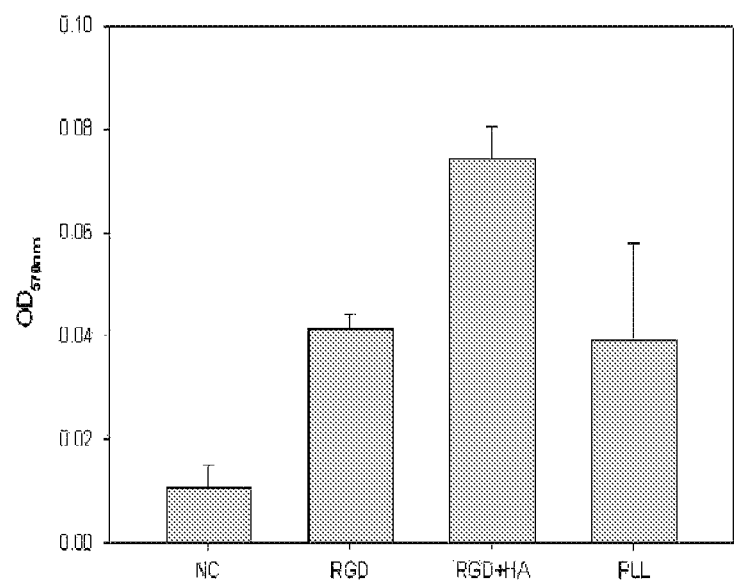
FIG. 22 is the result of performing cell adhesion, after a coacervate is prepared by using a mussel adhesive protein, fp-151-RGD and hyaluronic acid (17 kDa) and the surface is coated therewith.

Cell adhesive activity was measured in the same manner as in <Example 3-1>, except for using the coacervates formed in <Example 1-3>, and the results are shown in FIG. 22.

As shown in FIG. 22, coacervates formed by the mussel adhesive protein fp-151-RGD and hyaluronic acid (17 kDa) showed more excellent cell adhesive activity.

<3-3> Cell Adhesive Activity of Coacervate Formed by Mussel Adhesive Protein fp-131 and Hyaluronic Acid (17 kDa)

Figure 23:
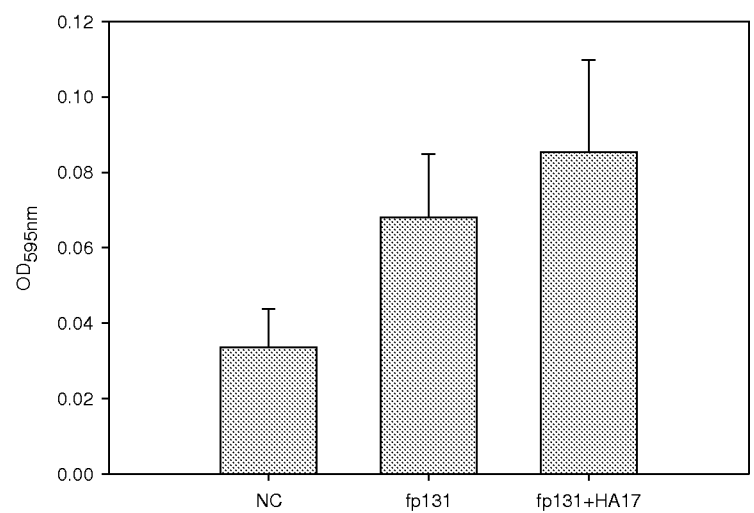
FIG. 23 is the result of performing cell adhesion, after a coacervate is prepared by using a mussel adhesive protein, fp-131 and hyaluronic acid (17 kDa) and the surface is coated therewith.

Cell adhesive activity was measured in the same manner as in <Example 3-1>, except for using the coacervates formed in <Example 1-2>, and the results are shown in FIG. 23.

As shown in FIG. 23, coacervates formed by the mussel adhesive protein fp-131 and hyaluronic acid (17 kDa) showed very excellent cell adhesive activity.

<3-4> Cell Adhesive Activity of Coacervate Formed by Mussel Adhesive Protein fp-151 and Hyaluronic Acid (35 kDa)

Figure 24:
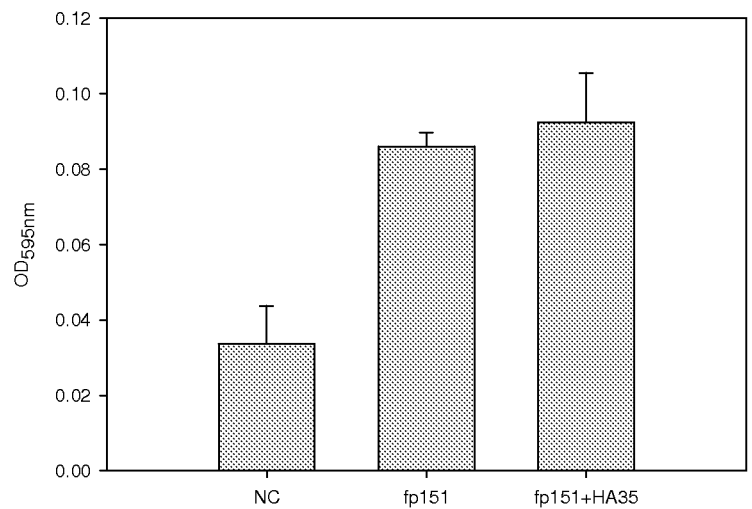
FIG. 24 is the result of performing cell adhesion, after a coacervate is prepared by using a mussel adhesive protein, fp-151 and hyaluronic acid (35 kDa) and the surface is coated therewith.

Cell adhesive activity was measured in the same manner as in <Example 3-1>, except for using the coacervates formed in <Example 1-4>, and the results are shown in FIG. 24.

As shown in FIG. 24, coacervates formed by the mussel adhesive protein fp-151 and hyaluronic acid (35 kDa) showed very excellent cell adhesive activity.

<3-5> Cell Adhesive Activity of Coacervate Formed by Mussel Adhesive Protein fp-151 and Hyaluronic Acid (59 kDa)

Figure 25:
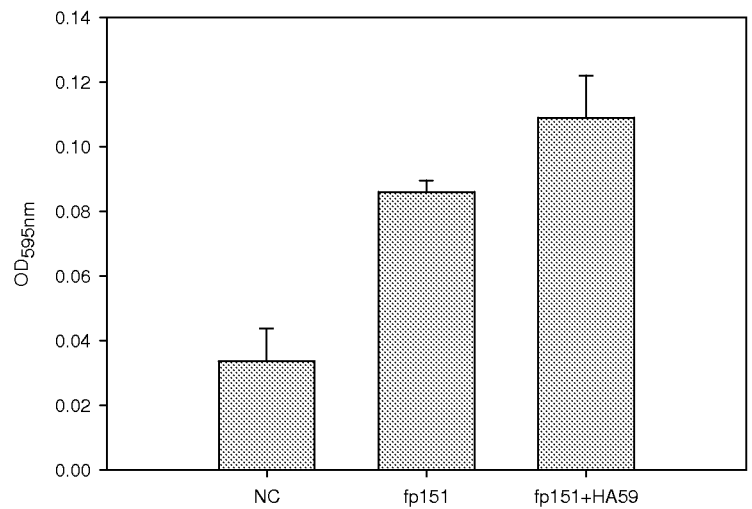
FIG. 25 is the result of performing cell adhesion, after a coacervate is prepared by using a mussel adhesive protein, fp-151 and hyaluronic acid (59 kDa) and the surface is coated therewith.

Cell adhesive activity was measured in the same manner as in <Example 3-1>, except for using the coacervates formed in <Example 1-5>, and the results are shown in FIG. 25.

As shown in FIG. 25, coacervates formed by the mussel adhesive protein fp-151 and hyaluronic acid (59 kDa) showed more excellent cell adhesive activity.

Example 4

Measurement of Adhesive Strength of Coacervate

<4-1> Measurement of Adhesive Strength of Coacervate Formed by Mussel Adhesive Protein fp-151 or fp-131 and Hyaluronic Acid (35 kDa) (Dry Condition)

The tyrosine residues of the mussel adhesive proteins, fp-151 and fp-131 were converted to DOPA by tyrosinase enzymatic reaction. Specifically, 5 µg/ml of mushroom-derived tyrosinase and 2 g/L of the protein were dissolved in PBS containing 25 mM ascorbic acid, and reacted at 37° C. for a half day, followed by dialysis with distilled water twice. The resultant was freeze-dried to obtain the modified mussel adhesive proteins, mfp-151 and mfp-131.

Each 10 g/L of mfp-151 and hyaluronic acid (35 kDa) was dissolved in 100 mM acetate buffer, of which pH was adjusted with sodium hydroxide to pH 3.8, and then the solutions were mixed with each other at a weight ratio of 8:2 to prepare coacervates. Liquid-phase colloidal coacervates condensed by centrifugation were applied and adhered to 12 mm×10 mm areas of aluminum surfaces. For comparison, the same concentration of BSA (bovine serum albumin) and the freeze-dried single mussel adhesive protein, mfp-151 or mfp-131 were dissolved in the same buffer, and adhered in the same manner, and dried for 24 hours at room temperature. A force was applied to both sides of the adhered aluminum sample to quantify a tensile strength of the adhesive using a tensile strength testing machine (Instron). The results are shown in FIG. 26.

Figure 26:
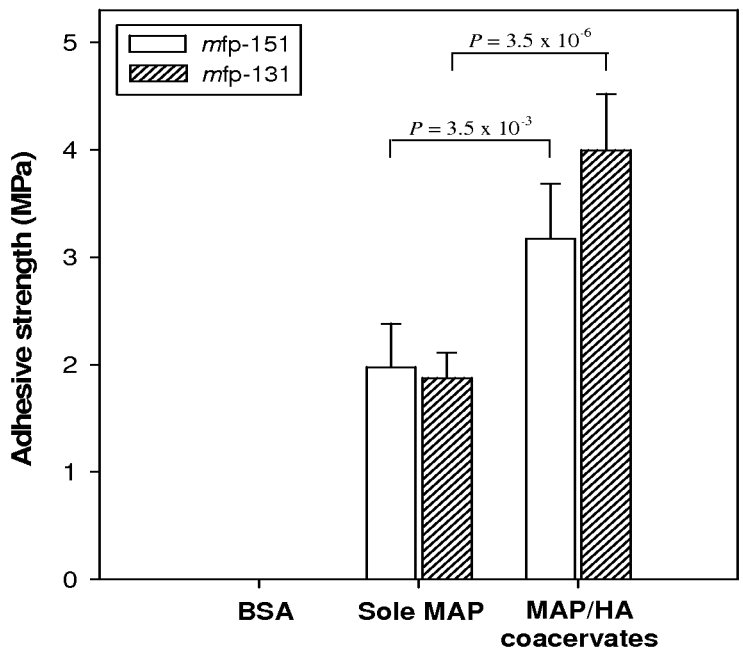
FIG. 26 is the result of comparing the adhesive strength under dry condition between a single mussel adhesive protein and coacervates prepared by using a mussel adhesive protein, mfp-151 and hyaluronic acid (35 kDa) and prepared by using a mussel adhesive protein, mfp-131 and hyaluronic acid (35 kDa)

As shown in FIG. 26, it can be seen that the coacervate formed by the mussel adhesive protein and hyaluronic acid has a more excellent adhesive strength than the single mussel adhesive protein.

<4-2> Measurement of Adhesive Strength of Coacervate Formed by Mussel Adhesive Protein fp-151 and Hyaluronic Acid (35 kDa or 59 kDa) (Wet Condition)

The coacervates formed by the mussel adhesive protein fp-151 and hyaluronic acid (35 kDa) in <Example 4-1> were mixed with a crosslinking agent tyrosinase at a weight ratio of tyrosinase to fp-151 of 1:200, or the coacervates formed by the mussel adhesive protein fp-151 and hyaluronic acid (59 kDa) in <Example 1-5> were mixed with glutaraldehyde at a volume of 0.5%, based on the total volume, and then applied and adhered to 10 mm×10 mm areas of aluminum surfaces. For comparison, fp-151 was dissolved in the same buffer, and the same amount of tyrosinase or glutaraldehyde was added thereto, and adhered in the same manner.

The sample was wrapped with gauze soaked in distilled water, and then wrapped in a plastic wrap to prevent dryness. It was left at 37° C. for 3 hours, and then a tensile strength of the adhesive was measured. The results are shown in FIG. 27.

Figure 27:
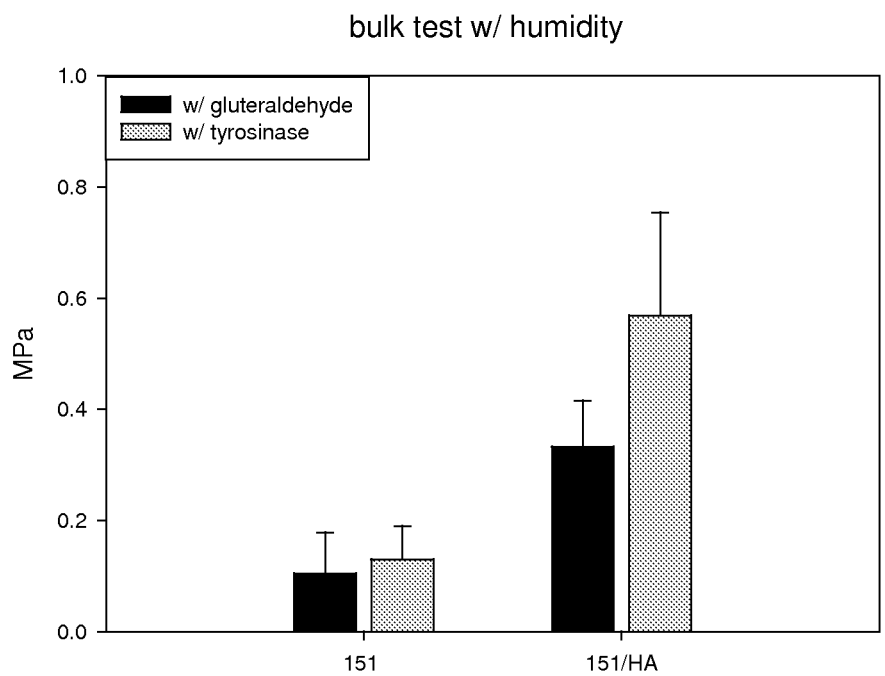
FIG. 27 is the result of comparing the adhesive strength under wet condition between a single mussel adhesive protein and a coacervate prepared by using a mussel adhesive protein, fp-151 and hyaluronic acid (35 kDa or 59 kDa) when tyrosinase and glutaraldehyde are added.

As shown in FIG. 27, it can be seen that the coacervate formed by the mussel adhesive protein and hyaluronic acid with addition of two crosslinking agents (tyrosinase, glutaraldehyde) has a more excellent adhesive strength than the single mussel adhesive protein.

<4-3> Measurement of Adhesive Strength of Coacervate Formed by Mussel Adhesive Protein fp-131 and Hyaluronic Acid (59 kDa) (Wet Condition)

In the same manner as in <Example 4-2>, the coacervates formed by the mussel adhesive protein fp-131 and hyaluronic acid (59 kDa) in <Example 1-11> were mixed with tyrosinase at a weight ratio of tyrosinase to fp-151 of 1:1000, or mixed with glutaraldehyde at a volume of 0.5%, based on the total volume, and then applied and adhered to 10 mm×10 mm areas of aluminum surfaces.

For comparison, fp-131 was dissolved in the same buffer, and the same amounts of tyrosinase and glutaraldehyde were added thereto, and adhered in the same manner. It was left at a temperature of 30° C. and humidity of 90% for 3 hours, and then a tensile strength of the adhesive was measured. The results are shown in FIG. 28.

Figure 28:
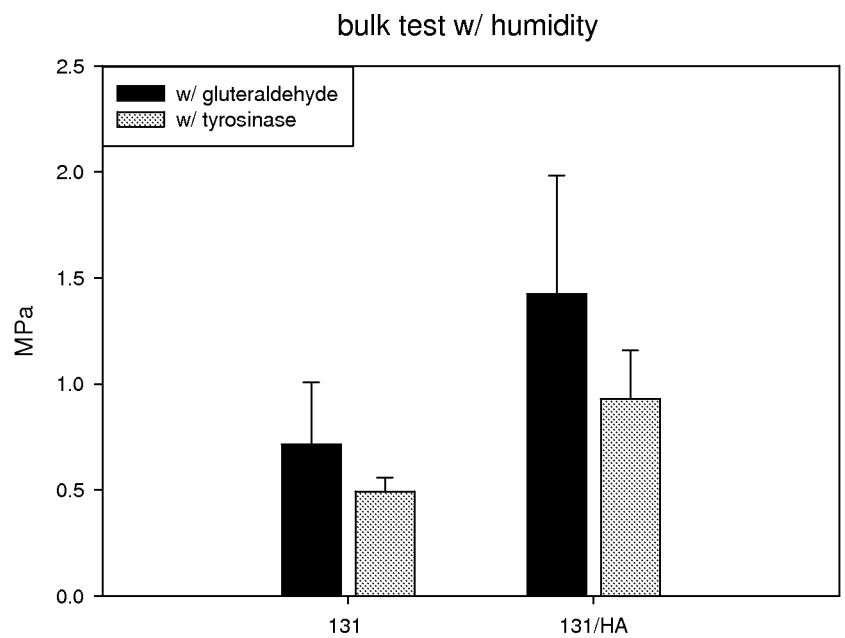
FIG. 28 is the result of comparing the adhesive strength under wet condition between a single mussel adhesive protein and a coacervate prepared by using a mussel adhesive protein, fp-131 and hyaluronic acid (59 kDa) when tyrosinase and glutaraldehyde are added.

As shown in FIG. 28, it can be seen that the coacervate formed by the mussel adhesive protein and hyaluronic acid with addition of two crosslinking agents (tyrosinase, glutaraldehyde) has a more excellent adhesive strength than the single mussel adhesive protein.

<4-4> Measurement of Adhesive Strength of Coacervate Formed by Mussel Adhesive Protein fp-151 and Hyaluronic Acid (59 kDa) (Under Water)

In the same manner as in <Example 4-2>, the coacervates formed by the mussel adhesive protein fp-151 and hyaluronic acid (59 kDa) in <Example 1-11> were mixed with tyrosinase at a weight ratio of tyrosinase to fp-151 of 1:1000, and mixed with glutaraldehyde at a volume of 0.5%, based on the total volume, and then applied and adhered to 10 mm×10 mm areas of aluminum surfaces.

For comparison, bovine serum albumin (BSA) was dissolved in the same buffer, and the same amounts of tyrosinase and glutaraldehyde were added thereto, and adhered in the same manner. It was immersed in PBS for 24 hours, and then a tensile strength of the adhesive was measured. The results are shown in FIG. 29.

Figure 29:
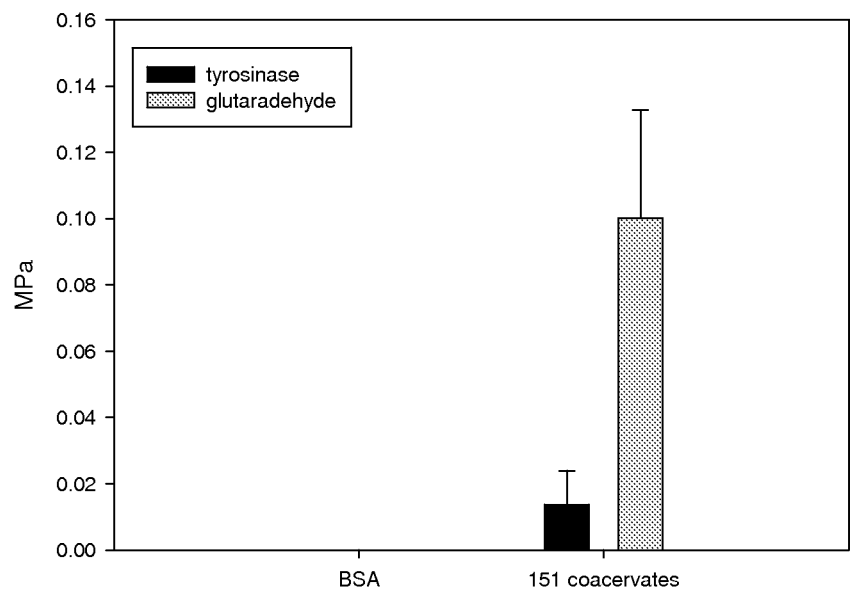
FIG. 29 is the result of comparing the adhesive strength under water between bovine serum albumin and a coacervate prepared by using a mussel adhesive protein, fp-151 and hyaluronic acid (59 kDa) when tyrosinase and glutaraldehyde are added.

As shown in FIG. 29, it can be seen that the coacervate formed by the mussel adhesive protein and hyaluronic acid with addition of two crosslinking agents (tyrosinase, glutaraldehyde) has a more excellent adhesive strength than BSA.

The invention claimed is:

1. A coacervate consisting of a mussel adhesive protein or a mutant thereof together with an anionic polymer.

2. The coacervate according to claim 1, wherein the mussel adhesive protein is one or more selected from
   (a) a polypeptide consisting of an amino acid sequence of SEQ ID NO. 4,
   (b) a polypeptide consisting of an amino acid sequence of SEQ ID NO. 5,
   (c) a polypeptide consisting of 1 to 10 consecutive amino acid sequences of SEQ ID NO. 6, and
   (d) a fusion polypeptide of two or more polypeptides selected from the group consisting of the polypeptides of (a), (b), and (c).

3. The coacervate according to claim 2, wherein the polypeptide of (c) consists of an amino acid sequence of SEQ ID NO. 7.

4. The coacervate according to claim 2, wherein the fusion polypeptide of (d) consists of an amino acid sequence of SEQ ID NO. 1 or SEQ ID NO. 3.

5. The coacervate according to claim 1, wherein the mutant of the mussel adhesive protein is a polypeptide linkage consisting of 3 to 25 amino acids including RGD at the carboxyl-terminus or amino-terminus of the mussel adhesive protein.

6. The coacervate according to claim 5, wherein the polypeptide including RGD is represented by an amino acid sequence selected from the group consisting of SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, and SEQ ID NO. 17.

7. The coacervate according to claim 5, wherein the mutant of the mussel adhesive protein is a polypeptide consisting of an amino acid sequence of SEQ ID NO. 2.

8. The coacervate according to claim 1, wherein 1% to 100% of the total number of tyrosine residues in the mussel adhesive protein is modified to 3,4-dihydroxyphenyl-L-alanine (DOPA).

9. The coacervate according to claim 1, wherein the anionic polymer is one or more selected from the group consisting of hyaluronic acid, ferredoxin, poly styrene sulfonic acid, gum arabic, gelatin, albumin, carbopol, high or low methoxyl pectin, sodium carboxymethyl guar gum, xanthan gum, whey protein, faba bean legumin, carboxymethyl cellulose, alginate, carrageenan, sodium hexametaphosphate, sodium casinate, hemoglobin, heparin and exopolysaccharide B40.

10. The coacervate according to claim 9, wherein the anionic polymer has an average molecular weight of 1 kpa to 300 kpa.

11. The coacervate according to claim 1, wherein the coacervate is formed by mixing the mussel adhesive protein and the anionic polymer at a weight ratio of 1:0.01 to 1:10.

12. The coacervate according to claim 1, wherein the coacervate is formed by mixing the mussel adhesive protein and the anionic polymer at pH 2.0 to pH 10.0.

13. An adhesive comprising the coacervate of claim 1.

14. The adhesive according to claim 13, wherein the adhesive is adhered to a substrate selected from the group consisting of plastic, glass, metal, and polymer synthetic resin.

15. The adhesive according to claim 13, wherein the adhesive is applied to a biological material.

16. The adhesive according to claim 13, wherein the adhesive is used in underwater adhesion.

17. The adhesive according to claim 13, further comprising one or more selected from the group consisting of surfactant, oxidant, crosslinking agent, and filler.

18. A composition for delivering bioactive materials, comprising the coacervate of claim 1.

19. The composition according to claim 18, wherein the coacervate is formed by mixing the mussel adhesive protein or the mutant thereof and the anionic polymer at pH 2.0 to pH 10.0 and a weight ratio of 1:0.01 to 1:10.

20. The composition according to claim 18, wherein the bioactive material is one or more selected from the group consisting of anticancer agents, antibiotics, anti-inflammatory agents, hormones, hormone antagonists, interleukins, interferons, heparin, enzymes, growth factors, tumor necrosis factors, endotoxins, lymphotoxins, urokinase, streptokinase, tissue plasminogen activators, protease inhibitors, alkylphosphocoline, radioactive isotopes, surfactants, cardiovascular pharmaceutic products, gastrointestinal pharmaceutic products, and neuropharmaceutic products.

21. A delivery vehicle for bioactive materials, wherein (a) the coacervate of claim 1 and a bioactive material are included, and (b) the bioactive material is encapsulated inside the coacervate.

22. The delivery vehicle for bioactive materials according to claim 21, wherein the delivery vehicle for bioactive materials is a microcapsule.

23. A method for preparing a delivery vehicle for bioactive materials, comprising the steps of:
    (a) mixing a mussel adhesive protein or a mutant thereof and a bioactive material, to form an emulsion and
    (b) adding an anionic polymer to the emulsion forming the coacervate of claim 1 encapsulating the bioactive material.

24. The method according to claim 23, wherein in step (a), the mussel adhesive protein or the mutant thereof and the anionic polymer are mixed at pH 2.0 to pH 10.0 and a weight ratio of 1:0.01 to 1:10.

25. The method according to claim 23, wherein the delivery vehicle for bioactive materials is a microcapsule.

26. A method for preparing the coacervate of claim 1, comprising the step of mixing a mussel adhesive protein or a mutant thereof with an anionic polymer at pH 2.0 to pH 10.0 and a weight ratio of 1:0.01 to 1:10.

27. A method for using the coacervate of claim 1 in adhesion, comprising the steps of:
    (a) preparing the coacervate claim 1 and
    (b) adhering the coacervate to a substrate.

* * * * *